(12) United States Patent
Adir et al.

(10) Patent No.: US 9,758,548 B2
(45) Date of Patent: Sep. 12, 2017

(54) ANTI-MICROBIAL PEPTIDES AND USES OF SAME

(75) Inventors: Noam Adir, Kiryat-Tivon (IL); Sharon Navon, Kiryat-Ata (IL); Tali Swartzmann, Kfar-Monash (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 14/116,851

(22) PCT Filed: May 10, 2012

(86) PCT No.: PCT/IL2012/050167
§ 371 (c)(1),
(2), (4) Date: Nov. 11, 2013

(87) PCT Pub. No.: WO2012/153337
PCT Pub. Date: Nov. 15, 2012

(65) Prior Publication Data
US 2014/0087997 A1 Mar. 27, 2014

Related U.S. Application Data

(60) Provisional application No. 61/484,691, filed on May 11, 2011.

(51) Int. Cl.
*A61K 38/06* (2006.01)
*A61K 38/07* (2006.01)
*A61K 38/08* (2006.01)
*C12Q 1/68* (2006.01)
*C07K 5/08* (2006.01)

(52) U.S. Cl.
CPC .............. *C07K 5/08* (2013.01); *A61K 38/06* (2013.01); *A61K 38/07* (2013.01); *A61K 38/08* (2013.01)

(58) Field of Classification Search
None
See application file for complete search history.

(56) References Cited

U.S. PATENT DOCUMENTS

| | | |
|---|---|---|
| 2003/0194445 A1 | 10/2003 | Kuhner et al. |
| 2004/0181033 A1* | 9/2004 | Han et al. ............. 530/324 |
| 2007/0027088 A1* | 2/2007 | Zabriskie et al. ......... 514/14 |
| 2010/0104607 A1 | 4/2010 | Engelberg-Kulka et al. |

FOREIGN PATENT DOCUMENTS

| | | | |
|---|---|---|---|
| CA | WO 2010060208 A1 * | 6/2010 | ............ A61K 39/39 |
| EP | 0503939 | 9/1992 | |
| GB | WO 2010004292 A1 * | 1/2010 | ......... A61K 39/0005 |
| WO | WO 01/98362 | 12/2001 | |
| WO | WO 2004085650 A1 * | 10/2004 | |
| WO | WO 2012/153337 | 11/2012 | |

OTHER PUBLICATIONS

Conotoxin Im12.10 (GenBank Accession No. ACV13215.1, accessed Nov. 30, 2014 at URL: ncbi.nlm.nih.gov/protein/256692957?report=genbank&log$=prottop&blast_rank=18&RID=7RV10UE7015).*
Zanetti et al., "Cathelicidins: a novel protein family with a common proregion and a variable C-terminal antimicrobial," FEBS Lett 374:1-5 (1995).*
Murray, et al., "Angiotensin Converting Enzyme Inhibitory Peptides Derived from Food Proteins: Biochemistry, Bioactivity and Production," Curr. Pharma. Design 13:773-791 (2007).*
Sinha et al., "Biodegradable microspheres for protein delivery," J. Contr. Rel. 90:261-280 (2003).*
Gregory et al., "Polypeptides. Part VIII.I Variations of the Aspartyl Position in the C-Terminal Tetrapeptide Amide Sequence of the Gastrins," J. Chem. Soc. (C) 715-725 (1968).*
Semenov et al., "A novel oxidation-labile linker for solid-phase peptide synthesis," Int. J. Peptide Prot. Res 45:303-304 (1995).*
Gogitidze et al., "Conformational Analysis of Cysteine-Containing Peptides and Prospects of Their Application to 213Bi Chelating in Antitumor Therapy," Russ. J. Bioorg. Chem. 32:240-247 (2006).*
International Preliminary Report on Patentability Dated Nov. 21, 2013 From the International Bureau of WIPO Re. Application No. PCT/IL2012/050167.
Communication Relating to the Results of the Partial International Search Dated Sep. 7, 2012 From the International Searching Authority Re. Application No. PCT/IL2012/050167.
International Search Report and the Written Opinion Dated Jan. 24, 2013 From the International Searching Authority Re. Application No. PCT/IL2012/050167.

* cited by examiner

*Primary Examiner* — Julie Ha
*Assistant Examiner* — Kristina M Hellman

(57) ABSTRACT

A method of treating a bacterial infection in a subject is disclosed. The method comprises administering to the subject a therapeutically effective amount of a peptide being between 3 and 5 amino acids, wherein at least one amino acid of the 3 and 5 amino acids is selected from the group consisting of tryptophan, cysteine, proline and methionine.

12 Claims, 41 Drawing Sheets
(35 of 41 Drawing Sheet(s) Filed in Color)

FIG. 2

$$F_R = \frac{N_X}{\sum_{i=1}^{n} N_{X_i}} \quad (1).$$

$$F_{Ex} = \frac{N_{A_i}}{\sum_{i=1}^{n} N_{A_i}} \times \frac{N_{A_j}}{\sum_{i=1}^{n} N_{A_i}} \times \frac{N_{A_k}}{\sum_{i=1}^{n} N_{A_i}} \quad (2).$$

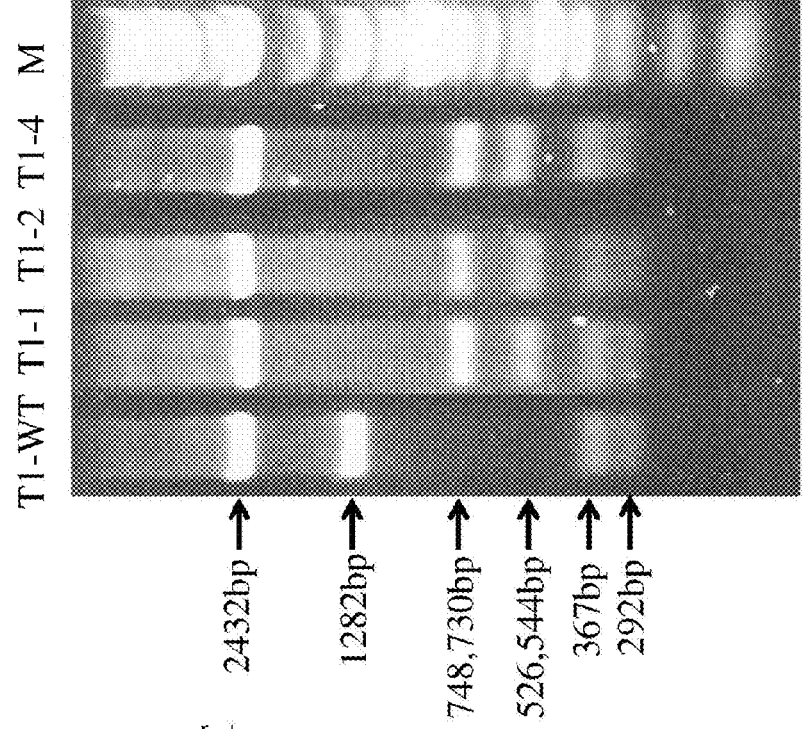
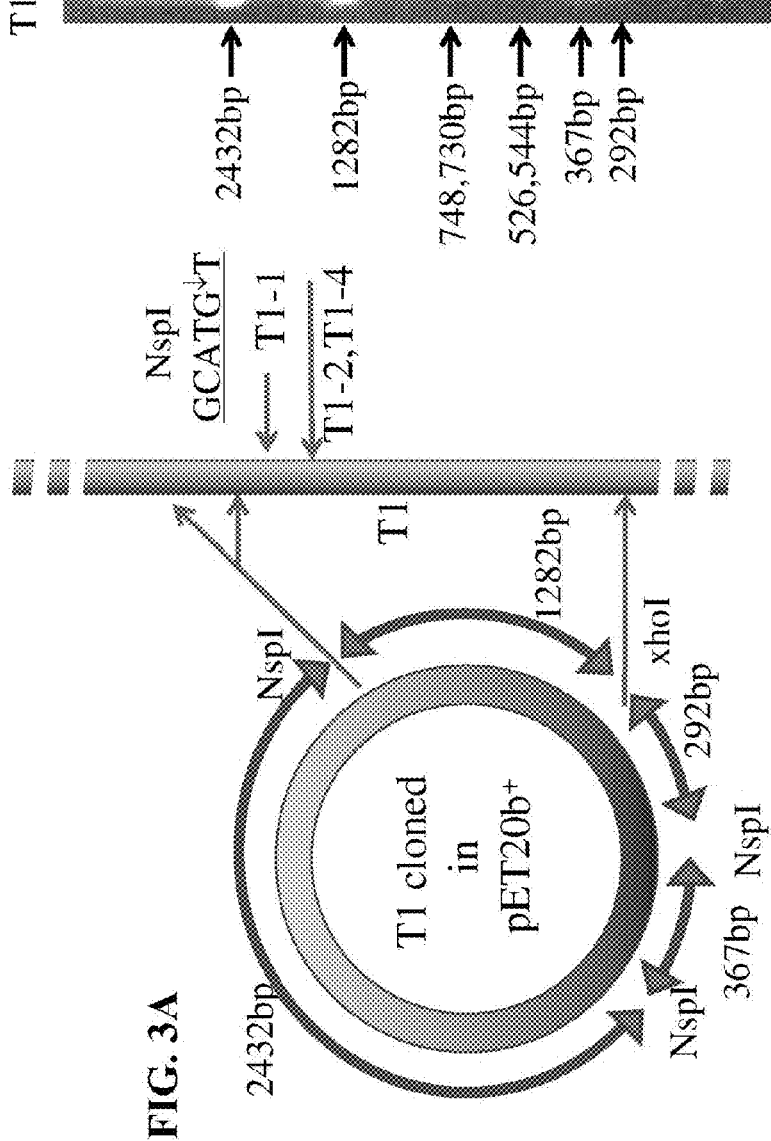
FIG. 3B
FIG. 3A

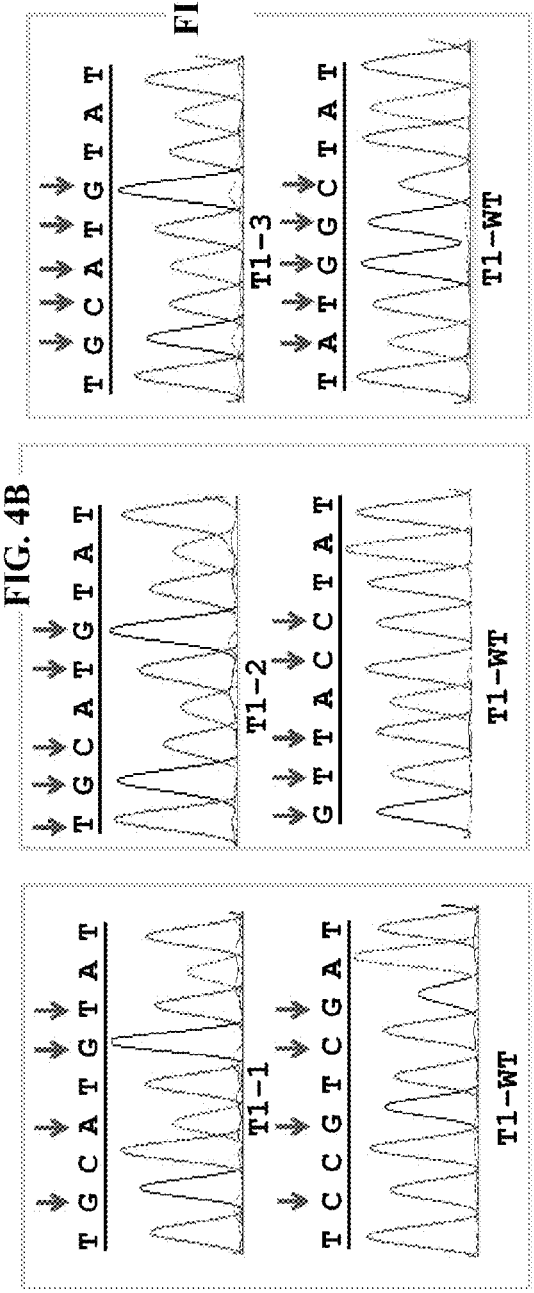

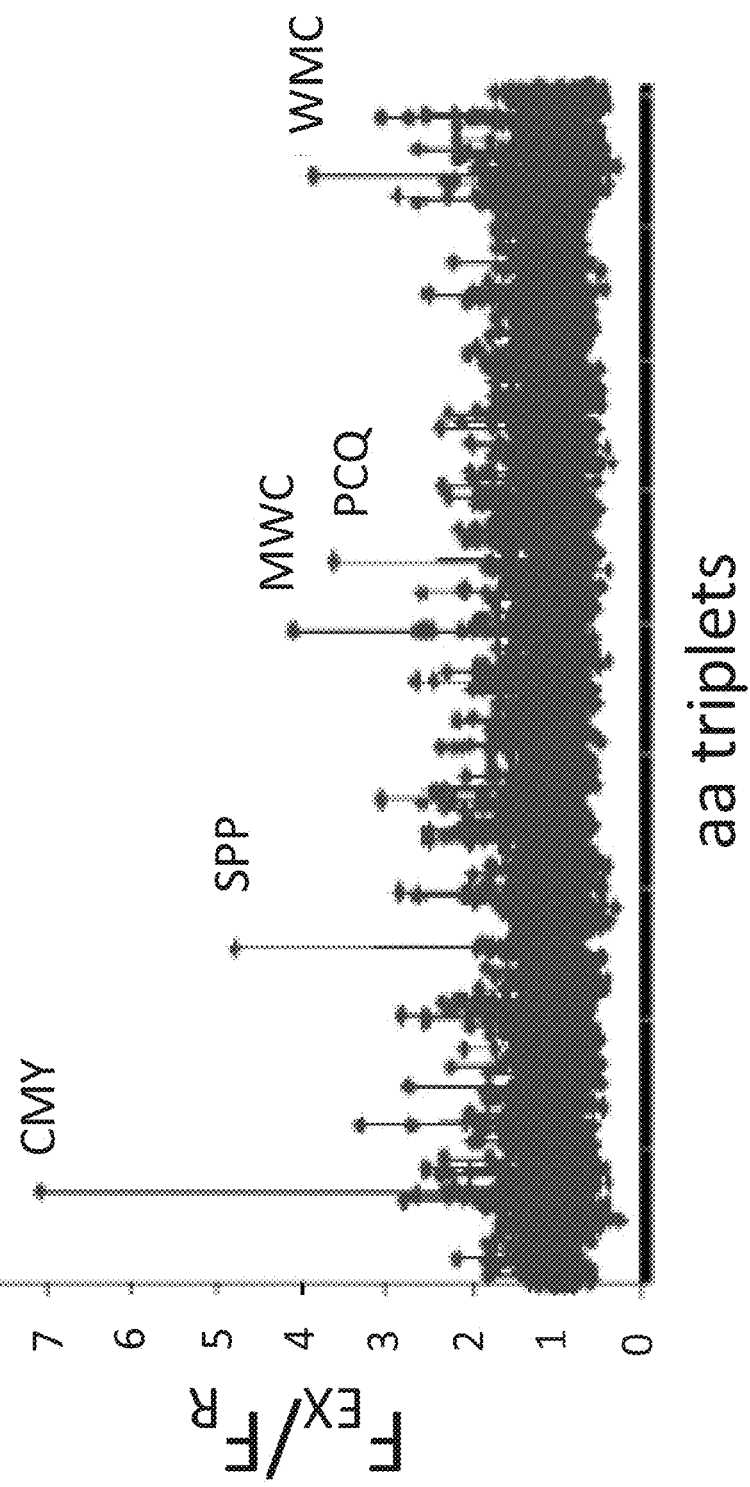

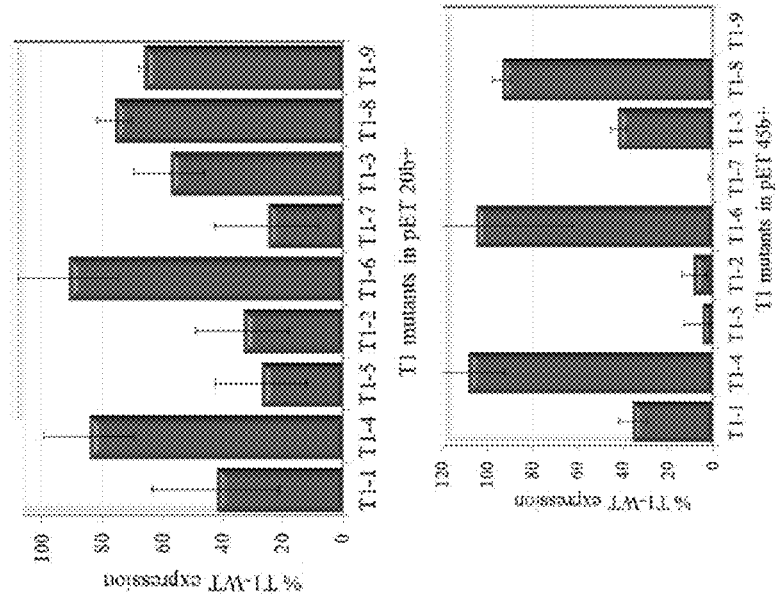
FIG. 5D
FIG. 5E
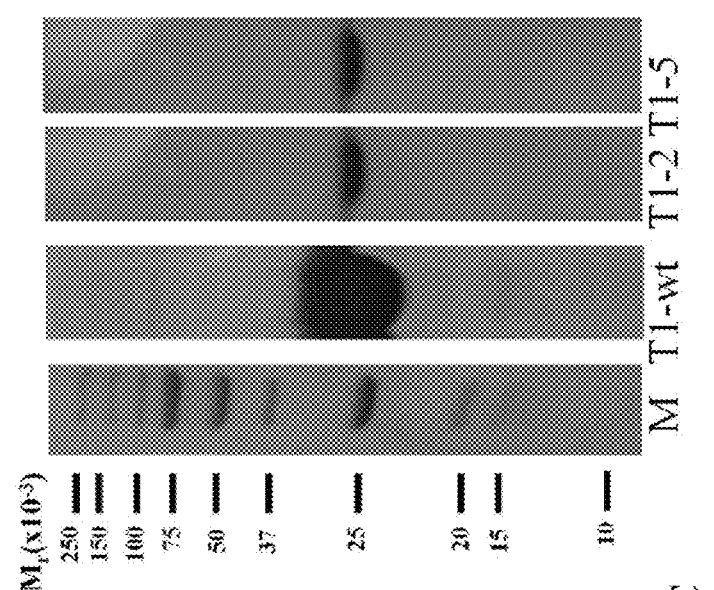
FIG. 5B
FIG. 5C

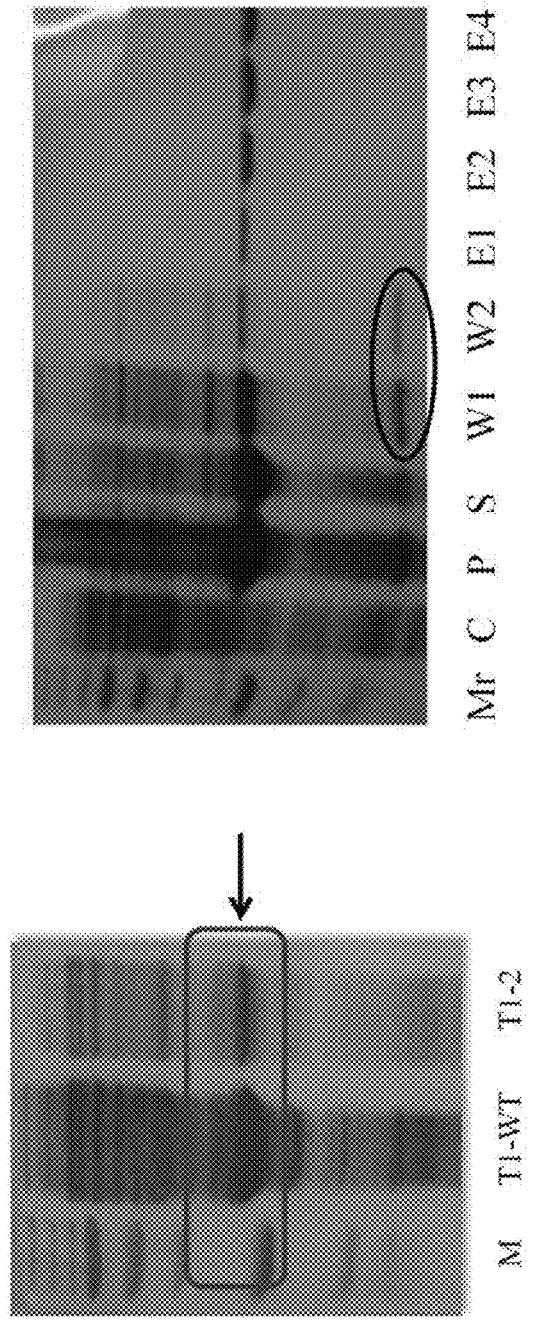

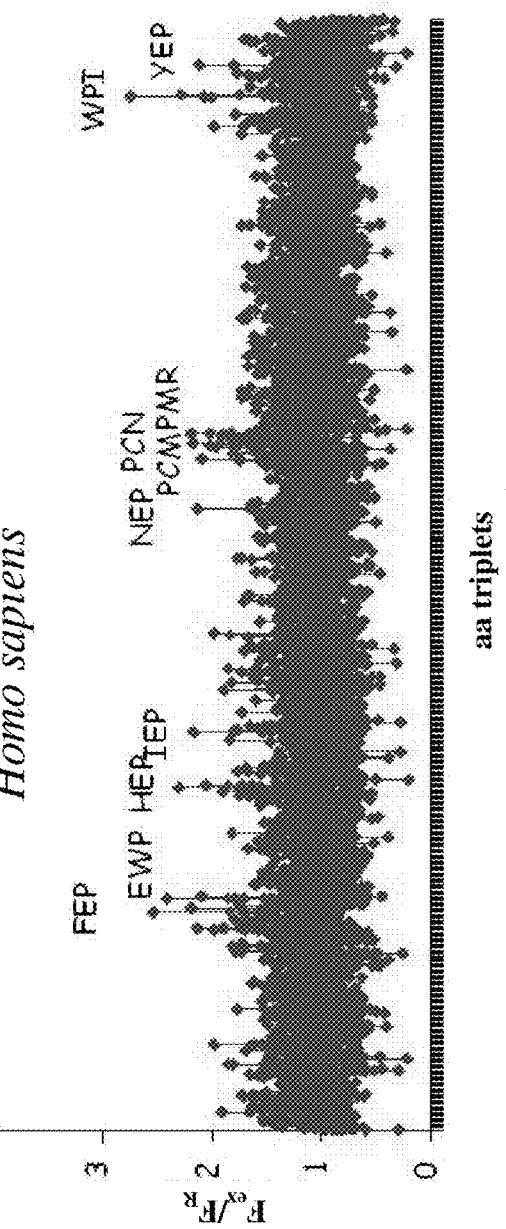

FIG. 9A T1- MntA:

MAATLSRLDISVDGVSVTYNNARLALYNATCTVEPGTITALVGPNGSGKSTLFKSIMGFLQPSQGRVRI
        CMY(T1-1)

GGFSVQKAQKQQLMAYVPQADEVDWNFPVSVFDVVM<u>GR</u>YGYMNVLRIPSAKDRRLVMESLERVGMVKY
    CMY(T1-2)                  MYC(T1-5)
    CMYW(T1-4)

RDRQIGELSGGQKKRAFLARALAQEGKVILLDEPFTGVDVKTEKGMIDLLMELRDEGHTILISTHDLAS
                                                  CMY(T1-3)

ISTFCDHTILLNRTILAQGKTEETFTKENLELTFGGLPMLSLNQMFESTEVDAHHHHHH

FIG. 9B T2-GFP

MTKGEELFTGVVPILVELDGDVNGHKFSVSGEGEGDATYGKLTLKFICTTGKLPVPWPTLVTTFSYGVQ
                                        CMY(T2-1)
                                        MYC(T2-2)

CFSRYPDHMKRHDFFKSAMPEGYVQERTIFFKDDGNYKTRAEVKFEGDTLVNRIELKGIDFKEDGNILG
HKLEYNYNSHNVYIMADKQKNGIKVNFKIRHNIEDGSVQLADHYQQNTPIGDPVLLPDNHYLSTQSAL
SKDPNEKRDHMVLLEFVTAAGITHGVDELYQPGGGSHHHHHH

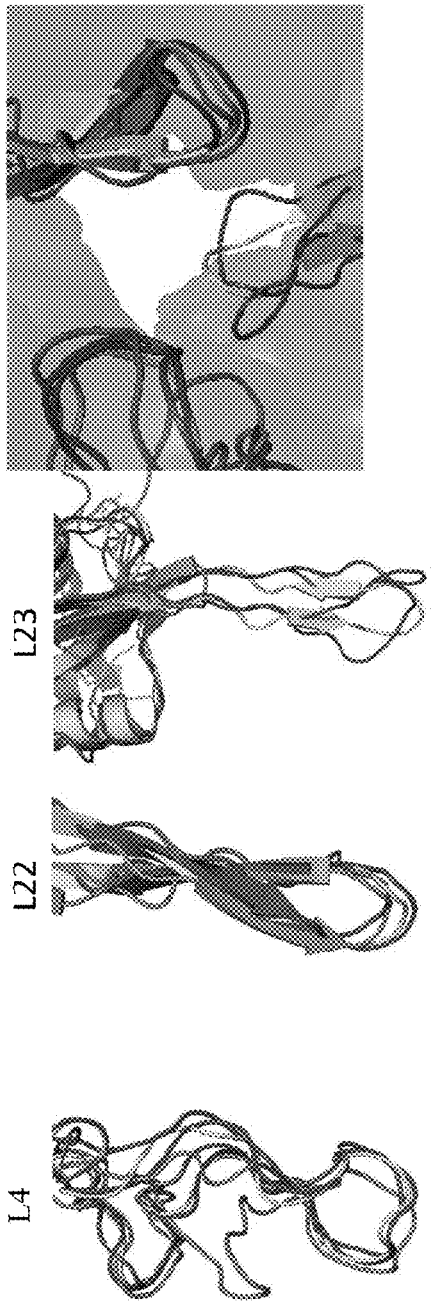

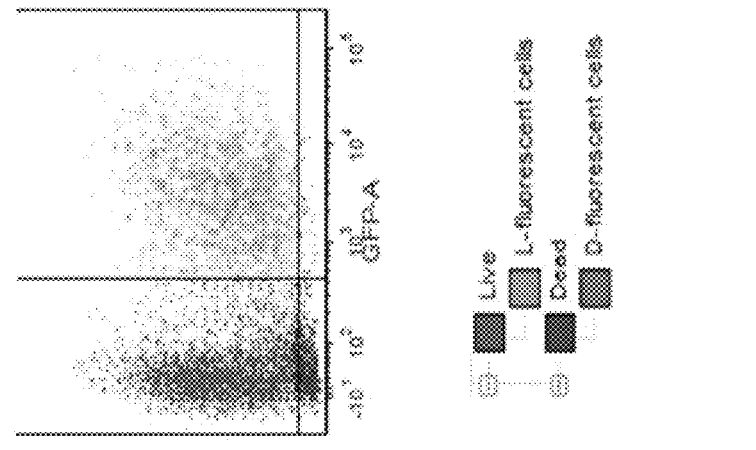
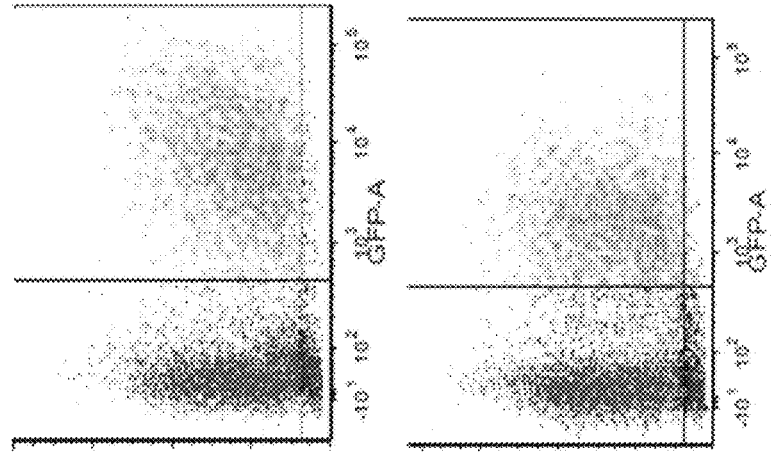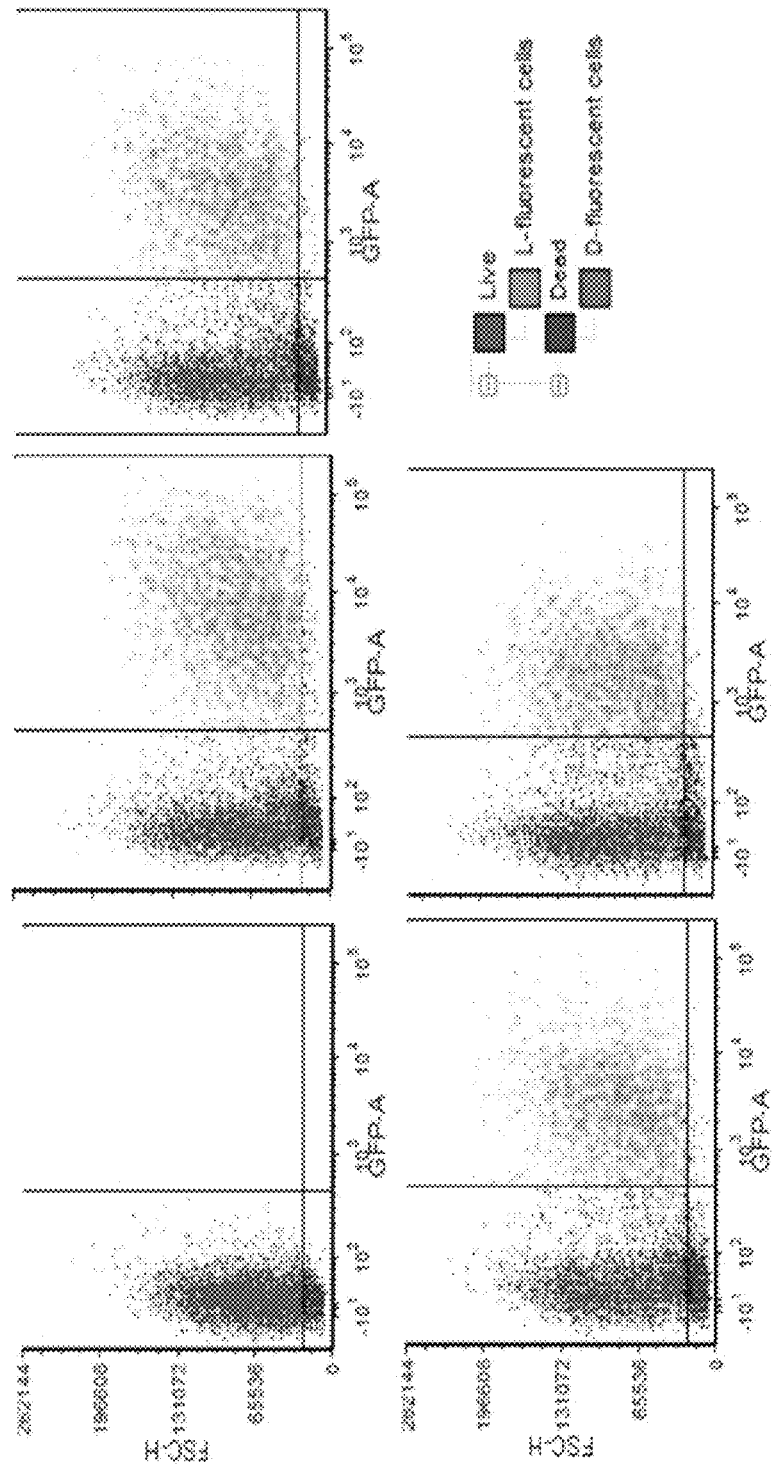

SEQUENCE LISTING

```
<160> NUMBER OF SEQ ID NOS: 42

<210> SEQ ID NO 1
<211> LENGTH: 266
<212> TYPE: PRT
<213> ORGANISM: Artificial sequence
<220> FEATURE:
<223> OTHER INFORMATION: T1- MntA wt polypeptide sequence

<400> SEQUENCE: 1

Met Ala Ala Thr Leu Ser Arg Leu Asp Ile Ser Val Asp Gly Val Ser
1               5                   10                  15

Val Thr Tyr Asn Asn Ala Arg Leu Ala Leu Tyr Asn Ala Thr Cys Thr
                20                  25                  30

Val Glu Pro Gly Thr Ile Thr Ala Leu Val Gly Pro Asn Gly Ser Gly
            35                  40                  45

Lys Ser Thr Leu Phe Lys Ser Ile Met Gly Phe Leu Gln Pro Ser Gln
        50                  55                  60

Gly Arg Val Arg Ile Gly Gly Phe Ser Val Gln Lys Ala Gln Lys Gln
65                  70                  75                  80

Gln Leu Met Ala Tyr Val Pro Gln Ala Asp Glu Val Asp Trp Asn Phe
                85                  90                  95
```

Pro Val Ser Val Phe Asp Val Val Met Met Gly Arg Tyr Gly Tyr Met
                100                 105                 110

Asn Val Leu Arg Ile Pro Ser Ala Lys Asp Arg Arg Leu Val Met Glu
            115                 120                 125

Ser Leu Glu Arg Val Gly Met Val Lys Tyr Arg Asp Arg Gln Ile Gly
130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
    210                 215                 220

Gln Gly Lys Thr Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His His
            260                 265

<210> SEQ ID NO 2
<211> LENGTH: 249
<212> TYPE: PRT
<213> ORGANISM: Artificial sequence
<220> FEATURE:
<223> OTHER INFORMATION: T2-GFP wt polypeptide sequence

<400> SEQUENCE: 2

Met Thr Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
         195                 200                 205

Lys Asp Pro Asn Glu Lys Arg Asp His Met Val Leu Leu Glu Phe Val
210                 215                 220

Thr Ala Ala Gly Ile Thr His Gly Val Asp Glu Leu Tyr Gln Pro Gly
225                 230                 235                 240

Gly Gly Ser His His His His His His
                245

<210> SEQ ID NO 3
<211> LENGTH: 266
<212> TYPE: PRT
<213> ORGANISM: Artificial sequence
<220> FEATURE:
<223> OTHER INFORMATION: T1-5 mutant sequence

<400> SEQUENCE: 3

Met Ala Ala Thr Leu Ser Arg Leu Asp Ile Ser Val Asp Gly Val Ser
1               5                   10                  15

Val Thr Tyr Asn Asn Ala Arg Leu Ala Leu Tyr Asn Ala Thr Cys Thr
                20                  25                  30

Val Glu Pro Gly Thr Ile Thr Ala Leu Val Gly Pro Asn Gly Ser Gly
            35                  40                  45

Lys Ser Thr Leu Phe Lys Ser Ile Met Gly Phe Leu Gln Pro Ser Gln
50                  55                  60

Gly Arg Val Arg Ile Gly Gly Phe Ser Val Gln Lys Ala Gln Lys Gln
65                  70                  75                  80

Gln Leu Met Ala Tyr Val Pro Gln Ala Asp Glu Val Asp Trp Asn Phe
                85                  90                  95

Pro Val Ser Val Phe Asp Val Val Met Met Trp Cys Tyr Gly Tyr Met
            100                 105                 110

Asn Val Leu Arg Ile Pro Ser Ala Lys Asp Arg Arg Leu Val Met Glu
        115                 120                 125

Ser Leu Glu Arg Val Gly Met Val Lys Tyr Arg Asp Arg Gln Ile Gly
130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
210                 215                 220

Gln Gly Lys Thr Glu Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His
            260                 265

<210> SEQ ID NO 4
<211> LENGTH: 49
<212> TYPE: DNA
<213> ORGANISM: Artificial sequence
<220> FEATURE:

<223> OTHER INFORMATION: Single strand DNA oligonucleotide

<400> SEQUENCE: 4
gcagccaccc tatctcgtct tgatatatgc atgtatggtg tcagcgtta                49

<210> SEQ ID NO 5
<211> LENGTH: 49
<212> TYPE: DNA
<213> ORGANISM: Artificial sequence
<220> FEATURE:
<223> OTHER INFORMATION: Single strand DNA oligonucleotide

<400> SEQUENCE: 5
taacgctgac accatacatg catatatcaa gacgagatag ggtggctgc                 49

<210> SEQ ID NO 6
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 6
gatatatccg tcgatggtgt cagctgcatg tataacaacg cccgtttggc cctt           54

<210> SEQ ID NO 7
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 7
aagggccaaa cgggcgttgt tatacatgca gctgacacca tcgacggata tatc           54

<210> SEQ ID NO 8
<211> LENGTH: 57
<212> TYPE: DNA
<213> ORGANISM: Artificial sequence
<220> FEATURE:
<223> OTHER INFORMATION: Single strand DNA oligonucleotide

<400> SEQUENCE: 8
gtttgatgtg gtgatgatgg ggcgctgcat gtatatgaat gtgttgcgta ttcctag        57

<210> SEQ ID NO 9
<211> LENGTH: 57
<212> TYPE: DNA
<213> ORGANISM: Artificial sequence
<220> FEATURE:
<223> OTHER INFORMATION: Single strand DNA oligonucleotide

<400> SEQUENCE: 9
ctaggaatac gcaacacatt catatacatg cagcgcccca tcatcaccac atcaaac        57

<210> SEQ ID NO 10
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 10
tccggcggtc aaaagaagcg ggcattttg atgtggtgtt tggcccagga aggcaagg        58

```
<210> SEQ ID NO 11
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 11
ccttgccttc ctgggccaaa caccacatca aaaatgcccg cttcttttga ccgccgga        58

<210> SEQ ID NO 12
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 12
tgatttggcc tccatttcca cctttttgtat gtatacaatt ctgctcaacc gcactatttt    60
ggccc                                                                 65

<210> SEQ ID NO 13
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 13
gggccaaaat agtgcggttg agcagaattg tatacataca aaaggtggaa atggaggcca    60
aatca                                                                 65

<210> SEQ ID NO 14
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 14
tgaagaactt ttcactggag ttgtctgcat gtatgttgaa ttagatggtg atgttaatgg    60
gcacaaa                                                               67

<210> SEQ ID NO 15
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 15
tttgtgccca ttaacatcac catctaattc aacatacatg cagacaactc cagtgaaaag    60
ttcttca                                                               67

<210> SEQ ID NO 16
<211> LENGTH: 72
<212> TYPE: DNA
<213> ORGANISM: Artificial sequence
<220> FEATURE:
<223> OTHER INFORMATION: Single strand DNA oligonucleotide

<400> SEQUENCE: 16
tgaagaactt ttcactggag ttgtcatgta ttgtgttgaa ttagatggtg atgttaatgg    60
```

```
gcacaaattt tc                                                          72
```

<210> SEQ ID NO 17
<211> LENGTH: 72
<212> TYPE: DNA
<213> ORGANISM: Artificial sequence
<220> FEATURE:
<223> OTHER INFORMATION: Single strand DNA oligonucleotide

<400> SEQUENCE: 17

```
gaaaatttgt gcccattaac atcaccatct aattcaacac aatacatgac aactccagtg      60
aaaagttctt ca                                                          72
```

<210> SEQ ID NO 18
<211> LENGTH: 7
<212> TYPE: PRT
<213> ORGANISM: Artificial sequence
<220> FEATURE:
<223> OTHER INFORMATION: A portion of TAT cell penetrating peptide

<400> SEQUENCE: 18

Tyr Gly Arg Lys Lys Arg Arg
1               5

<210> SEQ ID NO 19
<211> LENGTH: 11
<212> TYPE: PRT
<213> ORGANISM: Artificial sequence
<220> FEATURE:
<223> OTHER INFORMATION: A portion of TAT cell penetrating peptide

<400> SEQUENCE: 19

Tyr Gly Arg Lys Lys Arg Arg Gln Arg Arg Arg
1               5                   10

<210> SEQ ID NO 20
<211> LENGTH: 5
<212> TYPE: PRT
<213> ORGANISM: Artificial sequence
<220> FEATURE:
<223> OTHER INFORMATION: A portion of PTD cell penetrating peptide

<400> SEQUENCE: 20

Arg Arg Gln Arg Arg
1               5

<210> SEQ ID NO 21
<211> LENGTH: 61
<212> TYPE: PRT
<213> ORGANISM: Deinococcus radiodurans

<400> SEQUENCE: 21

Glu Val Val Thr Trp Gln Leu Ala Ser Arg Arg Arg Gly Thr Ala Ser
1               5                   10                  15

Thr Arg Thr Arg Ala Gln Val Ser Lys Thr Gly Arg Lys Met Tyr Gly
            20                  25                  30

Gln Lys Gly Thr Gly Asn Ala Arg His Gly Asp Arg Ser Val Pro Thr
        35                  40                  45

Phe Val Gly Gly Gly Val Ala Phe Gly Pro Lys Pro Arg
    50                  55                  60

<210> SEQ ID NO 22
<211> LENGTH: 61
<212> TYPE: PRT

<213> ORGANISM: Thermus thermophilus

<400> SEQUENCE: 22

Glu Val Val Arg Trp Gln Leu Ala Lys Arg Arg Gly Thr Ala Ser
1               5                   10                  15

Thr Lys Thr Arg Gly Glu Val Ala Tyr Ser Gly Arg Lys Ile Trp Pro
            20                  25                  30

Gln Lys His Thr Gly Arg Ala Arg His Gly Asp Ile Gly Ala Pro Ile
        35                  40                  45

Phe Val Gly Gly Gly Val Val Phe Gly Pro Lys Pro Arg
    50                  55                  60

<210> SEQ ID NO 23
<211> LENGTH: 61
<212> TYPE: PRT
<213> ORGANISM: Escherichia coli

<400> SEQUENCE: 23

Gln Val Val Ala Tyr Ala Ala Gly Ala Arg Gln Gly Thr Arg Ala
1               5                   10                  15

Gln Lys Thr Arg Ala Glu Val Thr Gly Ser Gly Lys Lys Pro Trp Arg
            20                  25                  30

Gln Lys Gly Thr Gly Arg Ala Arg Ser Gly Ser Ile Lys Ser Pro Ile
        35                  40                  45

Trp Arg Ser Gly Gly Val Thr Phe Ala Ala Arg Pro Gln
    50                  55                  60

<210> SEQ ID NO 24
<211> LENGTH: 74
<212> TYPE: PRT
<213> ORGANISM: Haloarcula marismortui

<400> SEQUENCE: 24

Lys Ala Val Arg Ala Ala Gln Ala Asn Arg Lys Gln Asp Tyr Gly Ser
1               5                   10                  15

Asp Glu Tyr Ala Gly Leu Arg Thr Pro Ala Glu Ser Phe Gly Ser Gly
            20                  25                  30

Arg Gly Gln Ala His Val Pro Lys Gln Asp Gly Arg Ala Arg Arg Val
        35                  40                  45

Pro Gln Ala Val Lys Gly Arg Ser Ala His Pro Lys Thr Glu Lys
    50                  55                  60

Asp Arg Ser Leu Asp Leu Asn Asp Lys Glu
65                  70

<210> SEQ ID NO 25
<211> LENGTH: 72
<212> TYPE: PRT
<213> ORGANISM: Deinococcus radiodurans

<400> SEQUENCE: 25

Ser Ala Ser Glu Pro Val Ala Lys Val Leu Asn Ser Ala Lys Ala Asn
1               5                   10                  15

Ala Leu His Asn Asp Glu Met Leu Glu Asp Arg Leu Phe Val Lys Glu
            20                  25                  30

Ala Tyr Val Asp Ala Gly Pro Thr Leu Lys Arg Leu Ile Pro Arg Ala
        35                  40                  45

Arg Gly Ser Ala Asn Ile Ile Lys Lys Arg Thr Ser His Ile Thr Ile
    50                  55                  60

-continued

Ile Val Ala Glu Lys Gly Asn Lys
65              70

<210> SEQ ID NO 26
<211> LENGTH: 72
<212> TYPE: PRT
<213> ORGANISM: Thermus thermophilus

<400> SEQUENCE: 26

Arg Gly Ala Tyr Phe Val Ala Lys Val Leu Glu Ser Ala Ala Ala Asn
1               5                   10                  15

Ala Val Asn Asn His Asp Met Leu Glu Asp Arg Leu Tyr Val Lys Ala
            20                  25                  30

Ala Tyr Val Asp Glu Gly Pro Ala Leu Lys Arg Val Leu Pro Arg Ala
        35                  40                  45

Arg Gly Arg Ala Asp Ile Ile Lys Lys Arg Thr Ser His Ile Thr Val
    50                  55                  60

Ile Leu Gly Glu Lys His Gly Lys
65              70

<210> SEQ ID NO 27
<211> LENGTH: 69
<212> TYPE: PRT
<213> ORGANISM: Escherichia coli

<400> SEQUENCE: 27

Lys Ala Ala Val Leu Val Lys Lys Val Leu Glu Ser Ala Ile Ala Asn
1               5                   10                  15

Ala Glu His Asn Asp Gly Ala Asp Ile Asp Asp Leu Lys Val Thr Lys
            20                  25                  30

Ile Phe Val Asp Glu Gly Pro Ser Met Lys Arg Ile Met Pro Arg Ala
        35                  40                  45

Lys Gly Arg Ala Asp Arg Ile Leu Lys Arg Thr Ser His Ile Thr Val
    50                  55                  60

Val Val Ser Asp Arg
65

<210> SEQ ID NO 28
<211> LENGTH: 72
<212> TYPE: PRT
<213> ORGANISM: Haloarcula marismortui

<400> SEQUENCE: 28

Lys Ala Ser Lys Ala Phe Leu Asp Leu Leu Gly Asn Ala Val Gly Asn
1               5                   10                  15

Ala Asp His Gln Gly Phe Asp Gly Glu Ala Met Thr Ile Lys His Val
            20                  25                  30

Ala Ala His Lys Val Gly Glu Gln Gln Gly Arg Lys Pro Arg Ala Met
        35                  40                  45

Gly Arg Ala Ser Ala Trp Asn Ser Pro Gln Val Asp Val Glu Leu Ile
    50                  55                  60

Leu Glu Glu Pro Glu Val Glu Asp
65              70

<210> SEQ ID NO 29
<211> LENGTH: 72
<212> TYPE: PRT
<213> ORGANISM: Deinococcus radiodurans

<400> SEQUENCE: 29

Val Tyr Ser Phe Trp Val Ser Pro Lys Ala Thr Lys Thr Glu Ile Lys
1               5                   10                  15

Asp Ala Ile Gln Gln Ala Phe Gly Val Arg Val Gly Ile Ser Thr
            20                  25                  30

Met Asn Val Pro Gly Lys Arg Lys Arg Val Gly Arg Phe Ile Gly Gln
                35                  40                  45

Arg Asn Asp Arg Lys Lys Ala Ile Val Arg Leu Ala Glu Gly Gln Ser
        50                  55                  60

Ile Glu Ala Leu Ala Gly Gln Ala
65                  70

<210> SEQ ID NO 30
<211> LENGTH: 72
<212> TYPE: PRT
<213> ORGANISM: Thermus thermophilus

<400> SEQUENCE: 30

Lys Tyr Thr Phe Trp Val His Pro Lys Ala Thr Lys Thr Glu Ile Lys
1               5                   10                  15

Asn Ala Val Glu Thr Ala Phe Lys Val Lys Val Val Lys Val Asn Thr
            20                  25                  30

Leu His Val Arg Gly Lys Lys Arg Leu Gly Arg Tyr Leu Gly Lys
        35                  40                  45

Arg Pro Asp Arg Lys Lys Ala Ile Val Gln Val Ala Pro Gly Gln Lys
        50                  55                  60

Ile Glu Ala Leu Glu Gly Leu Ile
65                  70

<210> SEQ ID NO 31
<211> LENGTH: 72
<212> TYPE: PRT
<213> ORGANISM: Escherichia coli

<400> SEQUENCE: 31

Thr Ile Val Leu Lys Val Ala Lys Asp Ala Thr Lys Ala Glu Ile Lys
1               5                   10                  15

Ala Ala Val Gln Lys Leu Phe Glu Val Glu Val Glu Val Val Asn Thr
            20                  25                  30

Leu Val Val Lys Gly Lys Val Lys Arg His Gly Gln Arg Ile Gly Arg
        35                  40                  45

Arg Ser Asp Trp Lys Lys Ala Tyr Val Thr Leu Lys Glu Gly Gln Asn
        50                  55                  60

Leu Asp Phe Val Gly Gly Ala Glu
65                  70

<210> SEQ ID NO 32
<211> LENGTH: 57
<212> TYPE: PRT
<213> ORGANISM: Haloarcula marismortui

<400> SEQUENCE: 32

Lys Leu Gln Phe Ala Val Asp Asp Arg Ala Ser Lys Gly Glu Val Ala
1               5                   10                  15

Asp Ala Val Glu Glu Gln Tyr Asp Val Thr Val Glu Gln Val Asn Thr
            20                  25                  30

Gln Asn Thr Met Asp Gly Glu Lys Lys Ala Val Val Arg Leu Ser Glu
        35                  40                  45

```
Asp Asp Asp Ala Gln Glu Val Ala Ser
        50                  55
```

<210> SEQ ID NO 33
<211> LENGTH: 266
<212> TYPE: PRT
<213> ORGANISM: Artificial sequence
<220> FEATURE:
<223> OTHER INFORMATION: T1-1 mutant sequence

<400> SEQUENCE: 33

```
Met Ala Ala Thr Leu Ser Arg Leu Cys Met Tyr Val Asp Gly Val Ser
1               5                   10                  15

Val Thr Tyr Asn Asn Ala Arg Leu Ala Leu Tyr Asn Ala Thr Cys Thr
            20                  25                  30

Val Glu Pro Gly Thr Ile Thr Ala Leu Val Gly Pro Asn Gly Ser Gly
        35                  40                  45

Lys Ser Thr Leu Phe Lys Ser Ile Met Gly Phe Leu Gln Pro Ser Gln
    50                  55                  60

Gly Arg Val Arg Ile Gly Gly Phe Ser Val Gln Lys Ala Gln Lys Gln
65                  70                  75                  80

Gln Leu Met Ala Tyr Val Pro Gln Ala Asp Glu Val Asp Trp Asn Phe
                85                  90                  95

Pro Val Ser Val Phe Asp Val Val Met Met Gly Arg Tyr Gly Tyr Met
            100                 105                 110

Asn Val Leu Arg Ile Pro Ser Ala Lys Asp Arg Arg Leu Val Met Glu
        115                 120                 125

Ser Leu Glu Arg Val Gly Met Val Lys Tyr Arg Asp Arg Gln Ile Gly
    130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
    210                 215                 220

Gln Gly Lys Thr Glu Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His His
            260                 265
```

<210> SEQ ID NO 34
<211> LENGTH: 266
<212> TYPE: PRT
<213> ORGANISM: Artificial sequence
<220> FEATURE:
<223> OTHER INFORMATION: T1-2 mutant sequence

<400> SEQUENCE: 34

```
Met Ala Ala Thr Leu Ser Arg Leu Asp Ile Ser Val Asp Gly Val Ser
1               5                   10                  15

Cys Met Tyr Asn Asn Ala Arg Leu Ala Leu Tyr Asn Ala Thr Cys Thr
            20                  25                  30
```

Val Glu Pro Gly Thr Ile Thr Ala Leu Val Gly Pro Asn Gly Ser Gly
            35                  40                  45

Lys Ser Thr Leu Phe Lys Ser Ile Met Gly Phe Leu Gln Pro Ser Gln
 50                  55                  60

Gly Arg Val Arg Ile Gly Gly Phe Ser Val Gln Lys Ala Gln Lys Gln
 65                  70                  75                  80

Gln Leu Met Ala Tyr Val Pro Gln Ala Asp Glu Val Asp Trp Asn Phe
                 85                  90                  95

Pro Val Ser Val Phe Asp Val Val Met Met Gly Arg Tyr Gly Tyr Met
                100                 105                 110

Asn Val Leu Arg Ile Pro Ser Ala Lys Asp Arg Arg Leu Val Met Glu
            115                 120                 125

Ser Leu Glu Arg Val Gly Met Val Lys Tyr Arg Asp Arg Gln Ile Gly
130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
210                 215                 220

Gln Gly Lys Thr Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His His
            260                 265

<210> SEQ ID NO 35
<211> LENGTH: 266
<212> TYPE: PRT
<213> ORGANISM: Artificial sequence
<220> FEATURE:
<223> OTHER INFORMATION: T1-4 mutant sequence

<400> SEQUENCE: 35

Met Ala Ala Thr Leu Ser Arg Leu Asp Ile Ser Val Asp Gly Val Ser
 1               5                  10                  15

Cys Met Tyr Trp Asn Ala Arg Leu Ala Leu Tyr Asn Ala Thr Cys Thr
                 20                  25                  30

Val Glu Pro Gly Thr Ile Thr Ala Leu Val Gly Pro Asn Gly Ser Gly
            35                  40                  45

Lys Ser Thr Leu Phe Lys Ser Ile Met Gly Phe Leu Gln Pro Ser Gln
 50                  55                  60

Gly Arg Val Arg Ile Gly Gly Phe Ser Val Gln Lys Ala Gln Lys Gln
 65                  70                  75                  80

Gln Leu Met Ala Tyr Val Pro Gln Ala Asp Glu Val Asp Trp Asn Phe
                 85                  90                  95

Pro Val Ser Val Phe Asp Val Val Met Met Gly Arg Tyr Gly Tyr Met
                100                 105                 110

Asn Val Leu Arg Ile Pro Ser Ala Lys Asp Arg Arg Leu Val Met Glu
            115                 120                 125

```
Ser Leu Glu Arg Val Gly Met Val Lys Tyr Arg Asp Arg Gln Ile Gly
    130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
210                 215                 220

Gln Gly Lys Thr Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His His
            260                 265

<210> SEQ ID NO 36
<211> LENGTH: 266
<212> TYPE: PRT
<213> ORGANISM: Artificial sequence
<220> FEATURE:
<223> OTHER INFORMATION: T1-3 mutant sequence

<400> SEQUENCE: 36

Met Ala Ala Thr Leu Ser Arg Leu Asp Ile Ser Val Asp Gly Val Ser
1               5                   10                  15

Val Thr Tyr Asn Asn Ala Arg Leu Ala Leu Tyr Asn Ala Thr Cys Thr
            20                  25                  30

Val Glu Pro Gly Thr Ile Thr Ala Leu Val Gly Pro Asn Gly Ser Gly
        35                  40                  45

Lys Ser Thr Leu Phe Lys Ser Ile Met Gly Phe Leu Gln Pro Ser Gln
50                  55                  60

Gly Arg Val Arg Ile Gly Gly Phe Ser Val Gln Lys Ala Gln Lys Gln
65                  70                  75                  80

Gln Leu Met Ala Tyr Val Pro Gln Ala Asp Glu Val Asp Trp Asn Phe
                85                  90                  95

Pro Val Ser Val Phe Asp Val Val Met Met Gly Arg Cys Met Tyr Met
            100                 105                 110

Asn Val Leu Arg Ile Pro Ser Ala Lys Asp Arg Arg Leu Val Met Glu
        115                 120                 125

Ser Leu Glu Arg Val Gly Met Val Lys Tyr Arg Asp Arg Gln Ile Gly
    130                 135                 140

Glu Leu Ser Gly Gly Gln Lys Lys Arg Ala Phe Leu Ala Arg Ala Leu
145                 150                 155                 160

Ala Gln Glu Gly Lys Val Ile Leu Leu Asp Glu Pro Phe Thr Gly Val
                165                 170                 175

Asp Val Lys Thr Glu Lys Gly Met Ile Asp Leu Leu Met Glu Leu Arg
            180                 185                 190

Asp Glu Gly His Thr Ile Leu Ile Ser Thr His Asp Leu Ala Ser Ile
        195                 200                 205

Ser Thr Phe Cys Asp His Thr Ile Leu Leu Asn Arg Thr Ile Leu Ala
210                 215                 220
```

```
Gln Gly Lys Thr Glu Glu Thr Phe Thr Lys Glu Asn Leu Glu Leu Thr
225                 230                 235                 240

Phe Gly Gly Leu Pro Met Leu Ser Leu Asn Gln Met Phe Glu Ser Thr
                245                 250                 255

Glu Val Asp Ala His His His His His His
            260                 265
```

<210> SEQ ID NO 37
<211> LENGTH: 249
<212> TYPE: PRT
<213> ORGANISM: Artificial sequence
<220> FEATURE:
<223> OTHER INFORMATION: T2-1 mutant sequence

<400> SEQUENCE: 37

```
Met Thr Lys Gly Glu Glu Leu Phe Thr Gly Val Val Cys Met Tyr Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Val Asp Glu Leu Tyr Gln Pro Gly
225                 230                 235                 240

Gly Gly Ser His His His His His His
                245
```

<210> SEQ ID NO 38
<211> LENGTH: 249
<212> TYPE: PRT
<213> ORGANISM: Artificial sequence
<220> FEATURE:
<223> OTHER INFORMATION: T2-2 mutant sequence

<400> SEQUENCE: 38

```
Met Thr Lys Gly Glu Glu Leu Phe Thr Gly Val Val Met Tyr Cys Val
```

```
                1               5                   10                  15
            Glu Leu Asp Gly Asp Val Asn Gly His Lys Phe Ser Val Ser Gly Glu
                            20                  25                  30
            Gly Glu Gly Asp Ala Thr Tyr Gly Lys Leu Thr Leu Lys Phe Ile Cys
                            35                  40                  45
            Thr Thr Gly Lys Leu Pro Val Pro Trp Pro Thr Leu Val Thr Thr Phe
                50                      55                  60
            Ser Tyr Gly Val Gln Cys Phe Ser Arg Tyr Pro Asp His Met Lys Arg
            65                      70                  75                  80
            His Asp Phe Phe Lys Ser Ala Met Pro Glu Gly Tyr Val Gln Glu Arg
                                85                  90                  95
            Thr Ile Phe Phe Lys Asp Asp Gly Asn Tyr Lys Thr Arg Ala Glu Val
                            100                 105                 110
            Lys Phe Glu Gly Asp Thr Leu Val Asn Arg Ile Glu Leu Lys Gly Ile
                            115                 120                 125
            Asp Phe Lys Glu Asp Gly Asn Ile Leu Gly His Lys Leu Glu Tyr Asn
                            130                 135                 140
            Tyr Asn Ser His Asn Val Tyr Ile Met Ala Asp Lys Gln Lys Asn Gly
            145                     150                 155                 160
            Ile Lys Val Asn Phe Lys Ile Arg His Asn Ile Glu Asp Gly Ser Val
                                165                 170                 175
            Gln Leu Ala Asp His Tyr Gln Gln Asn Thr Pro Ile Gly Asp Gly Pro
                            180                 185                 190
            Val Leu Leu Pro Asp Asn His Tyr Leu Ser Thr Gln Ser Ala Leu Ser
                            195                 200                 205
            Lys Asp Pro Asn Glu Lys Arg Asp His Met Val Leu Leu Glu Phe Val
                            210                 215                 220
            Thr Ala Ala Gly Ile Thr His Gly Val Asp Glu Leu Tyr Gln Pro Gly
            225                     230                 235                 240
            Gly Gly Ser His His His His His His
                            245
```

<210> SEQ ID NO 39
<211> LENGTH: 4
<212> TYPE: PRT
<213> ORGANISM: Artificial Sequence
<220> FEATURE:
<223> OTHER INFORMATION: anti-microbial peptides

<400> SEQUENCE: 39

Cys Met Tyr Trp
1

<210> SEQ ID NO 40
<211> LENGTH: 4
<212> TYPE: PRT
<213> ORGANISM: Artificial Sequence
<220> FEATURE:
<223> OTHER INFORMATION: anti-microbial peptides

<400> SEQUENCE: 40

Lys Lys Lys Lys
1

<210> SEQ ID NO 41
<211> LENGTH: 4
<212> TYPE: PRT
<213> ORGANISM: Artificial Sequence
<220> FEATURE:

```
<223> OTHER INFORMATION: anti-microbial peptides

<400> SEQUENCE: 41

Arg Arg Arg Arg
1

<210> SEQ ID NO 42
<211> LENGTH: 4
<212> TYPE: PRT
<213> ORGANISM: Artificial Sequence
<220> FEATURE:
<223> OTHER INFORMATION: anti-microbial peptides

<400> SEQUENCE: 42

Trp Cys Met Tyr
1
```

ANTI-MICROBIAL PEPTIDES AND USES OF SAME

RELATED APPLICATIONS

This application is a National Phase of PCT Patent Application No. PCT/IL2012/050167 having International filing date of May 10, 2012, which claims the benefit of priority under 35 USC §119(e) of U.S. Provisional Patent Application No. 61/484,691 filed on May 11, 2011. The contents of the above applications are all incorporated by reference as if fully set forth herein in their entirety.

SEQUENCE LISTING STATEMENT

The ASCII file, entitled 57253SequenceListing.txt, created on Aug. 18, 2013, comprising 33,196 bytes, submitted concurrently with the filing of this application is incorporated herein by reference.

FIELD AND BACKGROUND OF THE INVENTION

The present invention, in some embodiments thereof, relates to peptide agents comprising anti-microbial properties and to methods of treating diseases using same.

Before the evolution of adaptive immunity in higher vertebrates added complexity, specificity, and memory to fight microbial challenge, a simpler, non-specific ancient system of innate immunity evolved 2.6 billion years ago and continues to function as the principal defense for almost all living organisms. Innate immunity is necessarily rapid, cidal, redundant, and multifunctional. The antimicrobial function of innate immunity is mediated, in part, by small cationic peptides with potent antimicrobial activity against Gram-positive and Gram-negative bacteria, fungi, parasites, and some viruses. The principal mechanism of rapid killing of microbial pathogens is attributed to perturbation of the microbial cell membrane, but present understanding is incomplete and other mechanisms may also be operative. Human antimicrobial peptides (AMPs) such as defensins and cathelicidin (LL-37) are present in leukocytes and are also secreted by various epithelia in skin and mucosal surfaces including the ocular surface. In addition to their antimicrobial role, AMPs also serve as important effector molecules in inflammation, immune activation, and wound healing.

The driving force for the development of newer anti-infectives is almost always the inevitable emergence of bacterial resistance to antibiotics following widespread clinical, veterinary, and animal agriculture (growth promoter in chickens, pigs, and feedlot cattle) usage. The pharmaceutical industry has continuously met this need by modifying existing antibiotics and developing newer antibiotics in a timely fashion. These successful efforts have produced the wide variety of currently available drug classes of antibiotics [beta lactams (penicillins, carbapenems, cepahalosporins), glycopeptides, macrolides, ketolides, aminoglycosides, fluoroquinolones, oxazolidinones, and others]. Similarly, there have been dramatic successes in developing effective antivirals to kill important clinical viral pathogens (e.g., HIV, herpes viruses, and influenza). However, the rapid emergence of resistance is even a greater problem for life-threatening viral infections. The best example remains HIV, where the rapid emergence of resistance to single drugs posed daunting clinical problems. The only effective solution to this problem was to develop combination therapy involving several antivirals with different mechanisms of inhibitory action. Currently, there are 19 different approved drugs for anti-HIV therapy in use as components of combination therapy. They include (1) nucleoside reverse transcriptase inhibitors, (2) nucleotide reverse transcriptase inhibitors, (3) non-nucleoside reverse transcriptase inhibitors, (4) proteases, and (5) viral entry blockers inhibitors.

Despite the success to date in antimicrobial development, the inexorable, ongoing emergence of resistance worldwide continues to spur the search for novel anti-infectives to replace and/or supplement conventional antibiotics.

SUMMARY OF THE INVENTION

According to an aspect of some embodiments of the present invention there is provided a method of treating a bacterial infection in a subject in need thereof, the method comprising administering to the subject a therapeutically effective amount of a peptide being between 3 and 5 amino acids, wherein at least one amino acid of said 3 and 5 amino acids is selected from the group consisting of tryptophan, cysteine, proline and methionine, thereby treating the bacterial infection.

According to an aspect of some embodiments of the present invention there is provided a method of treating a bacterial infection in a subject in need thereof, the method comprising administering to the subject a therapeutically effective amount of a peptide comprising an amino acid sequence selected from the group consisting of CMYW (SEQ ID NO: 39), CMY, GPP, MWC, PCQ, WMC, CKF, MCM, WKC, YMC, CMW, CMY, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, CMY, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, KQP, DQS, IWP and HNK, the peptide being no longer than 5 amino acids, thereby treating the bacterial infection.

According to an aspect of some embodiments of the present invention there is provided an isolated anti-microbial peptide being between 3 and 5 amino acids, wherein at least one amino acid of the 3 and 5 amino acids is selected from the group consisting of tryptophan, cysteine, proline and methionine.

According to an aspect of some embodiments of the present invention there is provided an isolated anti-microbial peptide being between 3 and 5 amino acids, the peptide comprising an amino acid sequence selected from the group consisting of CMYW (SEQ ID NO: 39), CMY, GPP, MWC, PCQ, WMC, CKF, MCM, WKC, YMC, CMW, CMY, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, CMY, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, KQP, DQS, IWP and HNK.

According to an aspect of some embodiments of the present invention there is provided a molecule comprising the isolated peptide described herein, comprising a bacterial targeting moiety.

According to an aspect of some embodiments of the present invention there is provided a method of killing a microbe, the method comprising contacting the microbe with an isolated peptide comprising an amino acid sequence selected from the group consisting of CMYW (SEQ ID NO: 39), CMY, GPP, MWC, PCQ, WMC, CKF, MCM, WKC, YMC, CMW, CMY, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, CMY, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, KQP, DQS, IWP and HNK, the peptide being no longer than 5 amino acids, thereby killing the microbe.

According to an aspect of some embodiments of the present invention there is provided a solid support coated with the peptide described herein.

According to an aspect of some embodiments of the present invention there is provided an anti-bacterial composition, comprising a carrier and as an active ingredient the peptide described herein.

According to an aspect of some embodiments of the present invention there is provided a method of synthesizing an antimicrobial agent, comprising:
  (a) determining a frequency of a 3-5 amino acid sequence in an open reading frame (ORF) of a proteome of a microbe to obtain an actual frequency of the sequence;
  (b) multiplying a frequency of each individual amino acid of the 3-5 amino acid sequence in the ORF of the proteome of the microbe to obtain an expected frequency of the sequence;
  (c) comparing the actual frequency with the expected frequency, wherein a two fold reduction in the actual frequency compared to the expected frequency is indicative of a sequence of an antimicrobial agent; and
  (d) synthesizing the antimicrobial agent selected in step (c), thereby synthesizing the antimicrobial agent.

According to some embodiments of the invention, the peptide comprises an amino acid sequence selected from the group consisting of CMYW (SEQ ID NO: 39), CMY, GPP, MWC, PCQ, WMC, CKF, MCM, WKC, YMC, CMW, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, KQP and IWP.

According to some embodiments of the invention, the bacterial infection is induced by methicillin resistant *Staphylococcus aureus* or vancomycin resistant *Staphylococcus aureus*.

According to some embodiments of the invention, the isolated peptide is capable of blocking a ribosomal exit tunnel of a microorganism.

According to some embodiments of the invention, the isolated peptide comprises a cysteine residue and a methionine residue.

According to some embodiments of the invention, the isolated peptide comprises a cysteine residue and a tryptophan residue.

According to some embodiments of the invention, the isolated peptide comprises at least two cysteine residues, two tryptophan residues or two proline residues.

According to some embodiments of the invention, the isolated peptide comprises an amino acid sequence selected from the group consisting of CMYW (SEQ ID NO: 39), CMY, GPP, MWC, PCQ, WMC, CKF, MCM, WKC, YMC, CMW, CMY, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, CMY, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, IWP and KQP.

According to some embodiments of the invention, the isolated peptide is cyclic.

According to some embodiments of the invention, the isolated peptide is capable of killing a microbe selected from the group consisting of a bacteria, a fungus, a parasite a protozoa and an archaea.

According to some embodiments of the invention, the isolated peptide is antibacterial.

According to some embodiments of the invention, the isolated peptide is capable of killing a bacteria selected from the group consisting of *Escherichia coli* (*E. coli*), *Shigella*, *Salmonella*, *Campylobacter*, *Vibrio*, *Helicobacter*, *Streptococcus*, *Staphylococcus*, *Candida*, *Neisseria*, *Chlamydia*, *Pseudomonas*, *Klebsiella*, *Legionella*, *Listeria*, *Mycobacterium*, *Leishmenia*, *Heamophilus*, *Pseudomonas*, *Plasmodium*, *Bacillus*, *Mycoplasma*, *Rickettsia*, *D. radiodurans*, *H. marismortui* and *T. thermopholus*.

According to some embodiments of the invention, the bacteria comprise *E. coli*.

According to some embodiments of the invention, the bacteria peptide comprises a sequence selected from the group consisting of CMYW (SEQ ID NO: 39), CMY, GPP, MWC, PCQ and WMC.

According to some embodiments of the invention, the bacteria peptide comprises a CMYW (SEQ ID NO: 39) sequence.

According to some embodiments of the invention, the isolated peptide is attached to a sustained-release enhancing agent.

According to some embodiments of the invention, the sustained-release enhancing agent is selected from the group consisting of hyaluronic acid (HA), alginic acid (AA), polyhydroxyethyl methacrylate (Poly-HEMA), polyethylene glycol (PEG), glyme and polyisopropylacrylamide.

According to some embodiments of the invention, the contacting is effected in vivo.

According to some embodiments of the invention, the contacting is effected ex vivo.

According to some embodiments of the invention, the microbe comprises a bacteria.

According to some embodiments of the invention, the formulation of the composition is selected from the group consisting of a spray, a cream, a mouthwash, a wipe, a foam, a soap, an oil, a solution, a lotion, an ointment, a paste and a gel.

According to some embodiments of the invention, the carrier is a pharmaceutically acceptable carrier.

According to some embodiments of the invention, the method further comprises testing the agent for antimicrobial properties.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
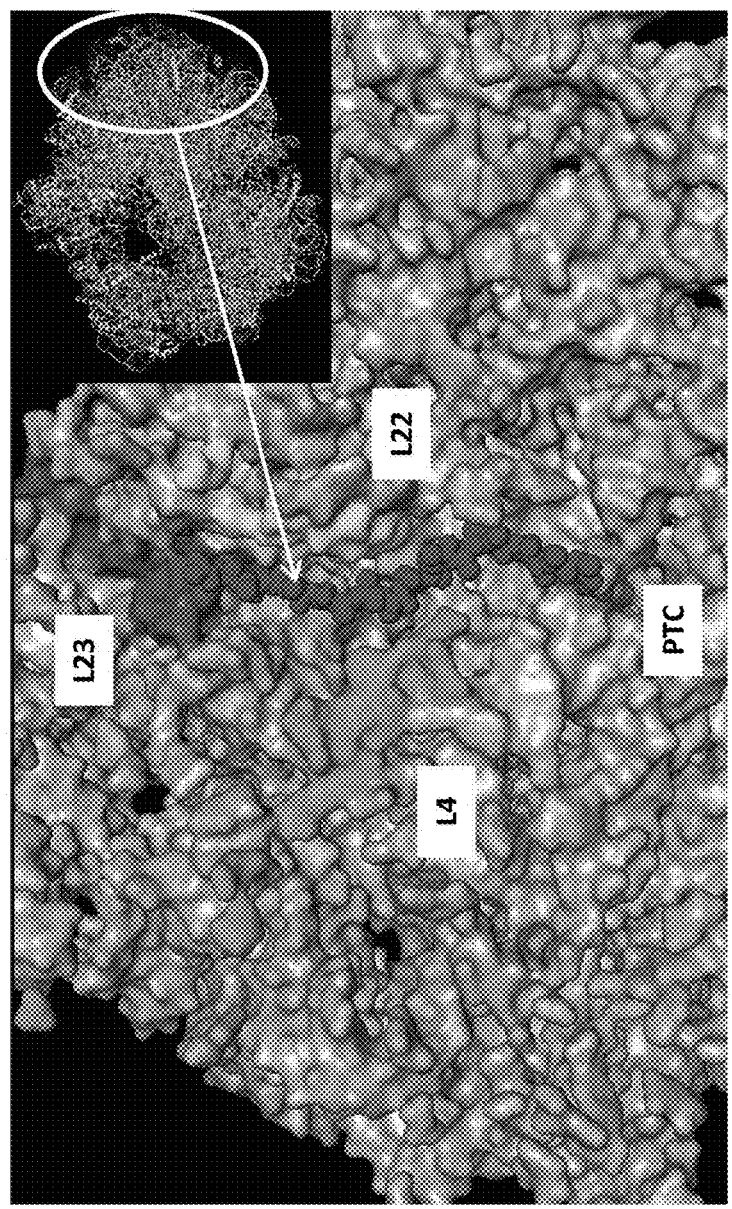

FIG. 1 is a molecular visualization of the ribosomal exit tunnel. The *E. coli* 50S ribosomal subunit (PDB code 3 cc2) was clipped to reveal the tunnel. The outline of the tunnel is filled with a mock polypeptide chain (magenta). The three proteins that extend into the tunnel L4, L22 and L23 are shown in surface representation (yellow, green and red, respectively). The inset shows the entire 70S *E. coli* ribosome, with the white oval showing the position of the exit from the tunnel. PTC, peptidyl transferase center.

FIG. 2 presents the equations used for the method of URS calculation. In order to identify URSs a program was developed that calculates the ratio of actual frequency of a specific sequence ($F_R$) divided by the expected frequency of the sequence ($F_{EX}$). $F_R$ was obtained by counting the number of times ($N_x$) each specific sequence of amino acids (3-5 aa) is present in the database which is then divided by the total number of sequences in the data base ($\Sigma N_{Xi}$, Eq 1). The actual prevalence of each of the aa in the sequence ($N_{Ai}/\Sigma N_{Ai}$) were multiplied to obtain the expected frequency ($F_{EX}$) for each sequence (Eq 2).

FIGS. 3A-B illustrate PCR analysis to verify the mutation presence. The plasmids of T1-WT, T1-1, T1-2 and T1-3 mutants were digested by NspI and XhoI restrict enzymes. NspI cuts the plasmid in three different locations, while XhoI cuts it just once. The theoretical fragments length of T1-WT are: 2432 pb, 1282 bp, 376 bp, 292 pb. Mutagenesis causes the insertion of additional NspI site in the mutants T1-1, T1-2 and T1-4. This results in the cleavage of the 1282 bp fragment into either 730 and 544 bp fragments (T1-1) or 748 bp and 526 bp fragments (T1-2 and T1-4).

FIGS. 4A-F are graphs illustrating sequence analysis of the URS mutants. Mutated nucleotides are marked with the red arrow. The wild-type sequence is given for comparison. A. T1-1, B. T1-2, C. T1-3, D. T1-4, E. T2-1, F. T2-2.

FIGS. 5A-K illustrate information related to the under-represented triplet sequences (URSs) described herein.

FIG. 5A is a plot illustrating identification of *E. coli* URSs. The ratio of expected appearance to actual appearance ($N_{ex}/N_r$) of all $8.33 \times 10^7$ triplets in the 29 redundant proteomes of *E. coli* used in this study clearly identifies significant URSs. See Methods for details on the method used for URS calculation.

FIGS. 5B-E are graphs and photographs illustrating that embedded URSs inhibit translation in vivo. A. SDS-PAGE analysis of Target 1 proteins (wt, T1-2, T1-5) expressed in BL-21(DE3)pLysS cells for four hours and purified by chelation chromatography. Purification was performed from equal cell numbers. B. Immunoblot of isolated Target 1 proteins (from an equal number of cells) using anti-His$_6$ antibodies. Panel A and B are Representative of at least four independent experiments for each mutant. Quantification of target-1 mutant protein expression in pET20b+ expression vector compared to WT. D. Quantification of target-1 mutant protein expression in pET45b+ expression vector compared to WT. The two vectors used have different expression kinetics. Results shown in C and D are the mean±s.d from 4 independent experiments.

Figure 5F:
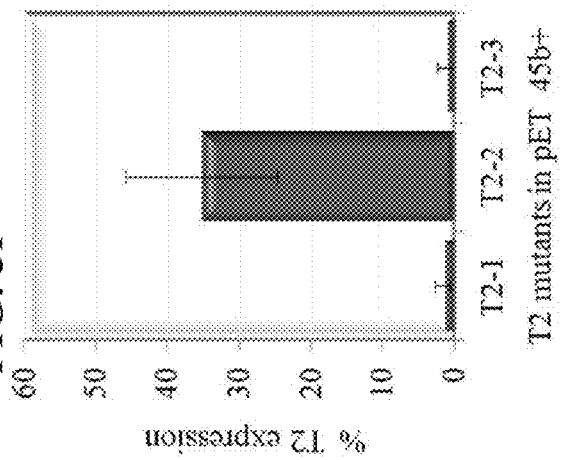

FIG. 5F illustrates that embedded URSs inhibit translation in vitro. Immunoblot of Target-1 wt and mutants produced using an in vitro transcription/translation system. The results are representative of four independent experiments.

Figure 5G:
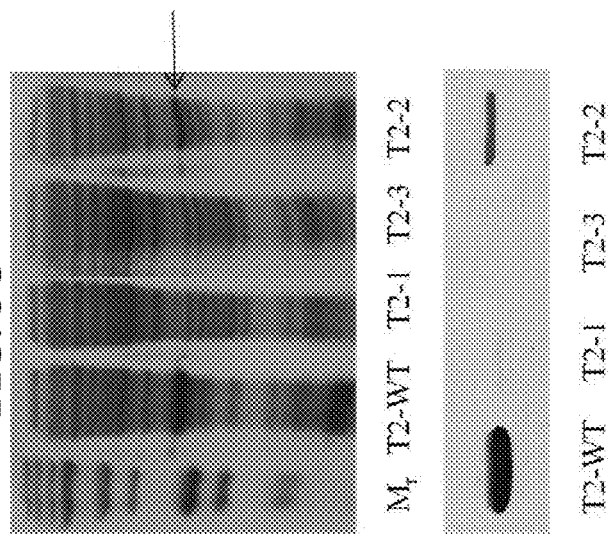
Figure 5H:
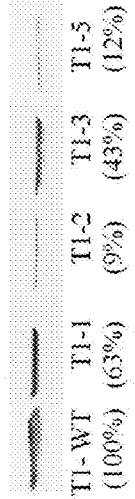
Figure 5I:
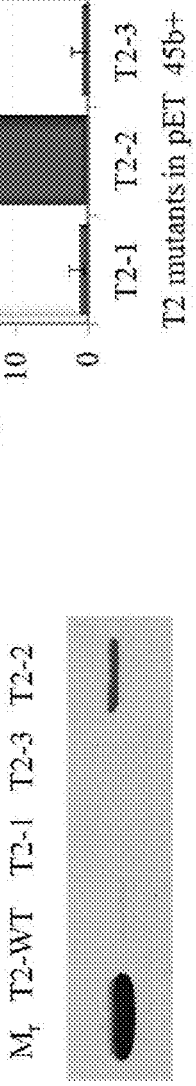

FIGS. 5G-I illustrate that embedded URSs inhibit translation of the target 2 protein in vivo. G. SDS-PAGE analysis of Target 2 proteins (wt, T2-2, T2-2, T2-3) expressed in BL-21(DE3)pLysS cells for four hours. Representative of four independent experiments. The arrow indicates the position of the mature target 2 protein. H. Immunoblot of Target 2 proteins using anti-His$_6$ antibodies. I. Quantification of target-2 mutant protein expression compared to T2-wt. Results shown in I are the mean±s.d from four independent experiments.

FIG. 5J illustrates that an embedded URS in T1 inhibits all protein translation. Whole cell SDS-PAGE analysis of BL-21 cells expressing T1-wt or T1-2 proteins for 3.5 hours. Equal cells were used for sample preparation. In addition to the decrease in the amount of the T1 protein that is expressed due to the presence of the embedded URS, there is a general decrease in protein synthesis, indicating an inhibition of ribosome recycling. The arrow indicates the position of the target 1 protein.

FIG. 5K illustrates that truncated peptides appear due to translational arrest. SDS-PAGE analysis of expression of T1-10. Following expression, protein was passed through the chelation column as in FIG. 5A. C, cells; P, inclusion body pellet; S, 8M urea dissolution of inclusion body pellet; W1 and W2, washes of chelation column; E1-E4, elution of bound fraction. The black oval shows a 12 kDa protein that does not bind to the column which is not seen in T1-wt analysis.

Figure 6:
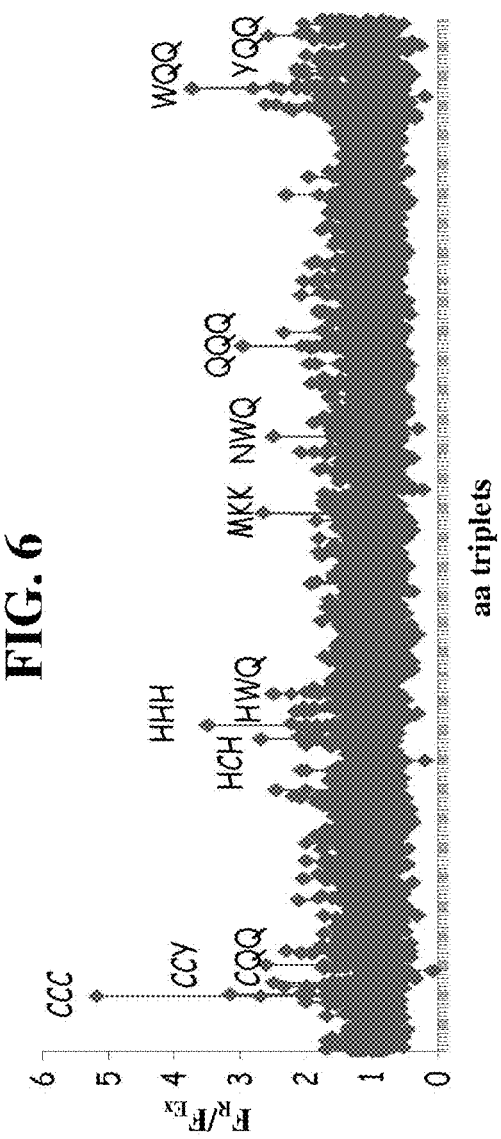

FIG. 6 is a graph illustrating over-represented triplet sequences (ORSs) in the *E. coli* proteomes. The graph shows the opposite ratio compared to FIG. 5A, thus outliers are sequences that are found more often than expected. Notice the presence of CCC, CCY and WQQ showing that the relative scarcity of a certain amino acid (such as C or W) is not the reason for URSs existence.

FIG. 7 is a graph illustrating URSs in the human proteome. The human URSs do not include those found in *E. coli* proteomes.

Figure 8A:
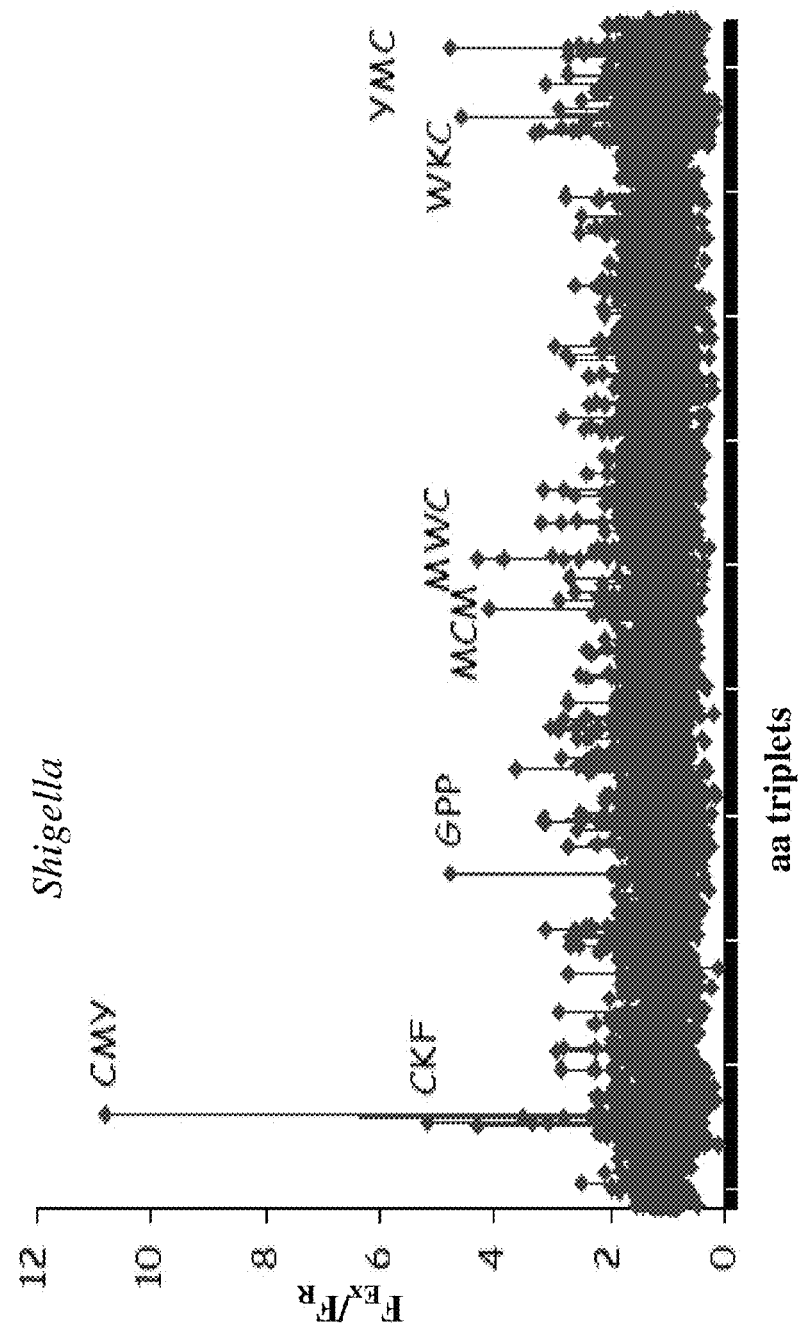
Figure 8B:
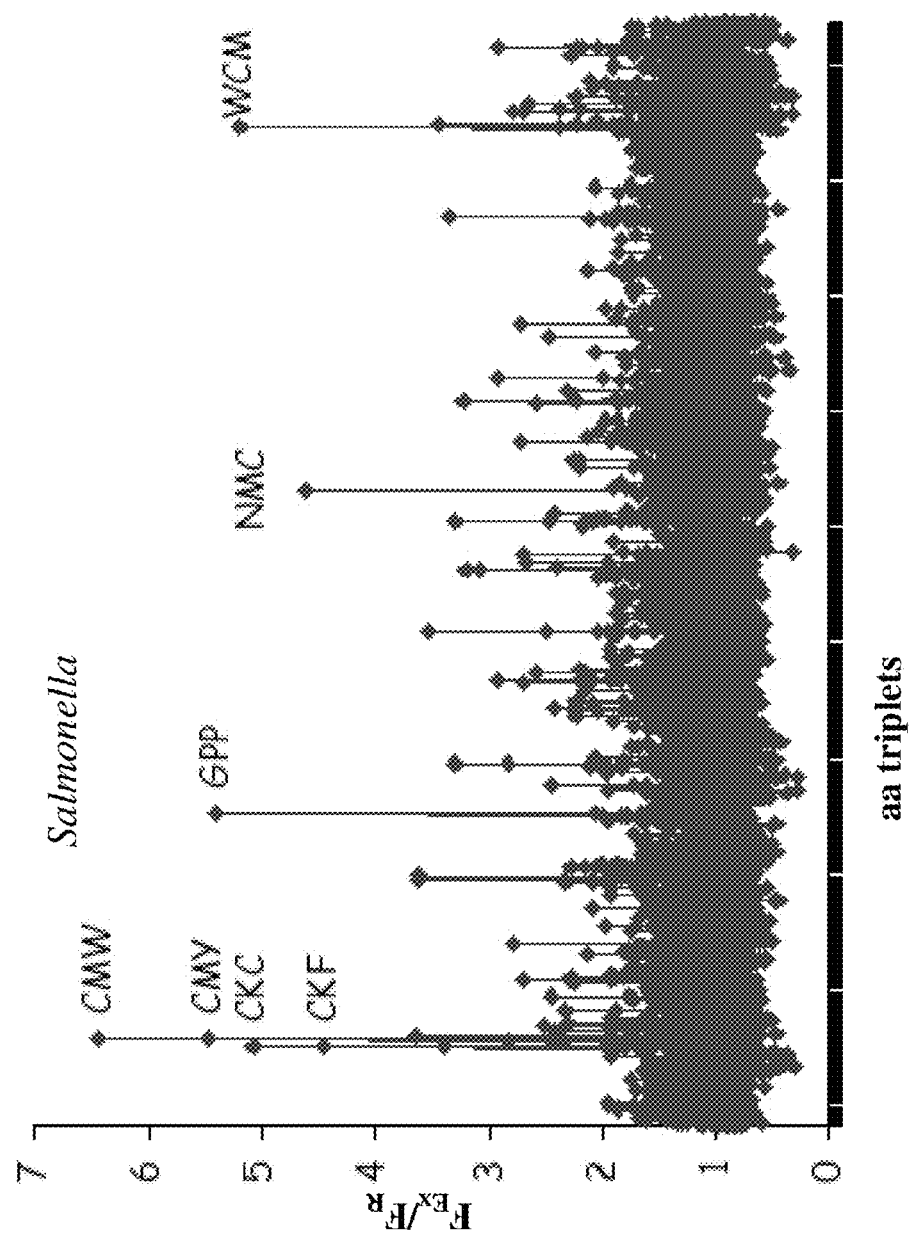
Figure 8C:
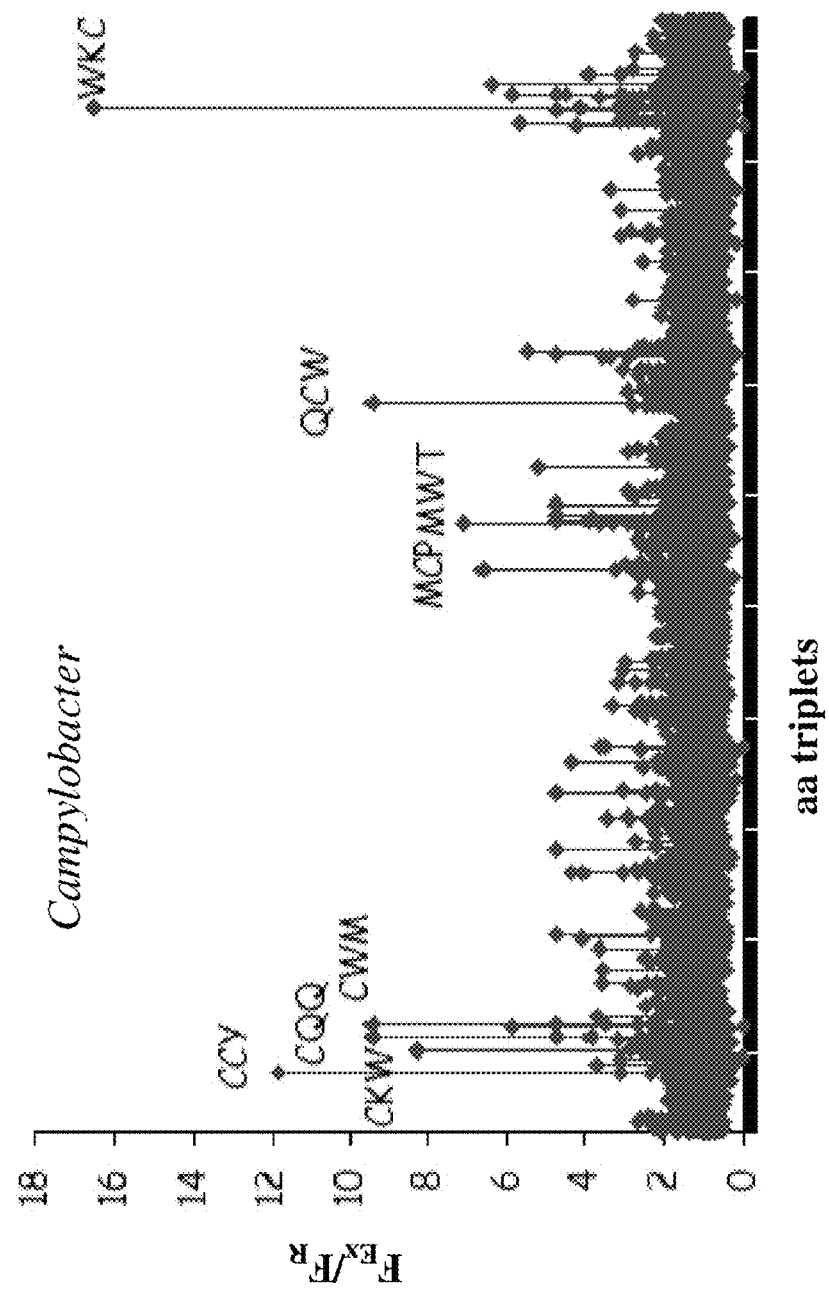
Figure 8D:
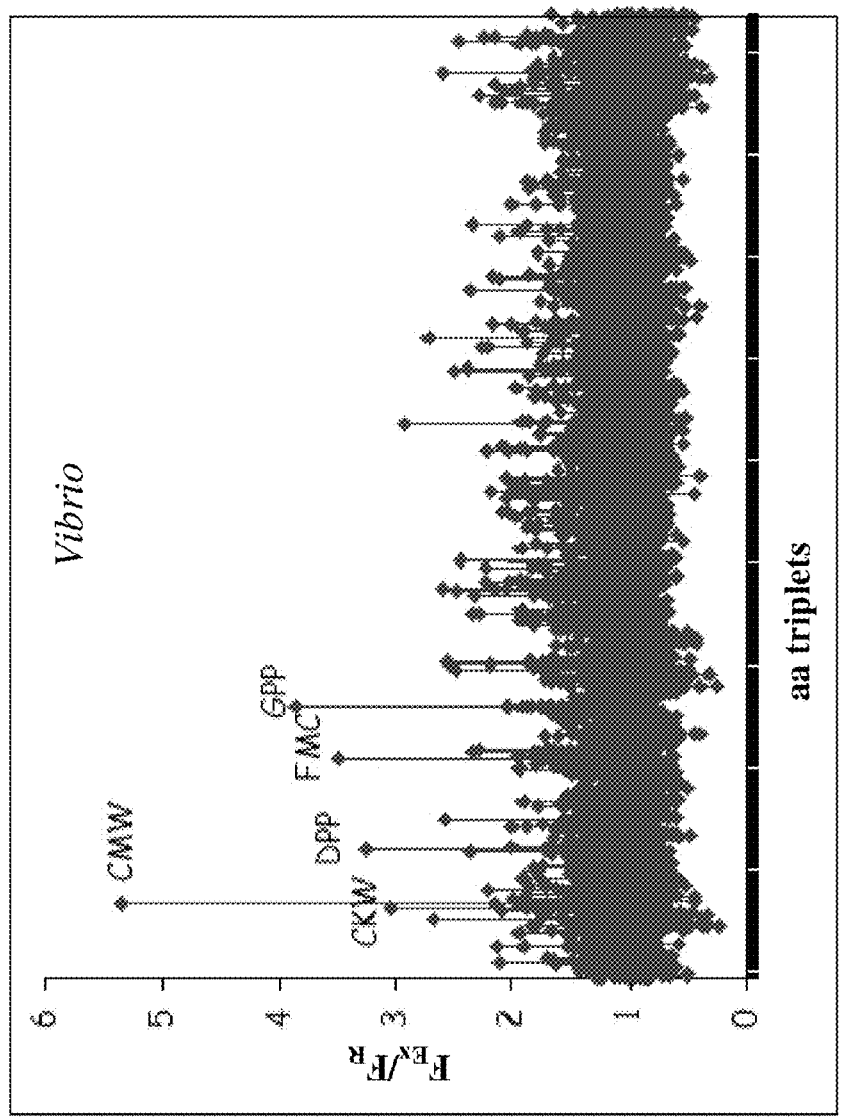
Figure 8E:
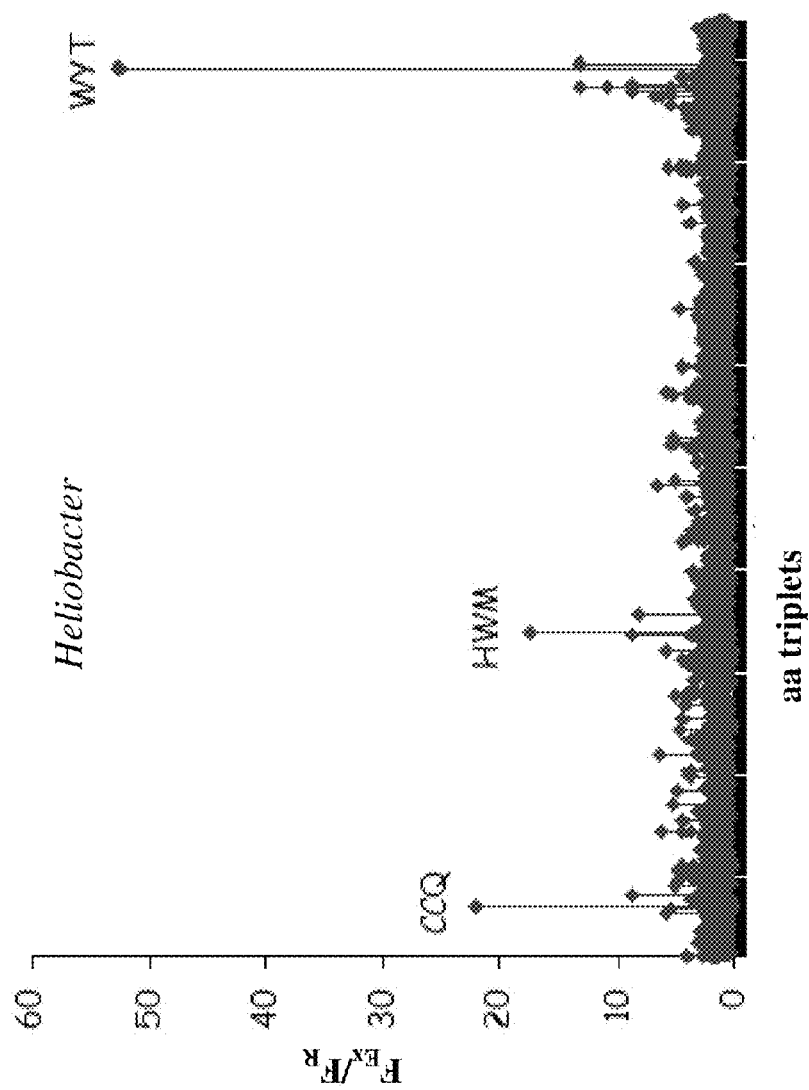
Figure 8F:
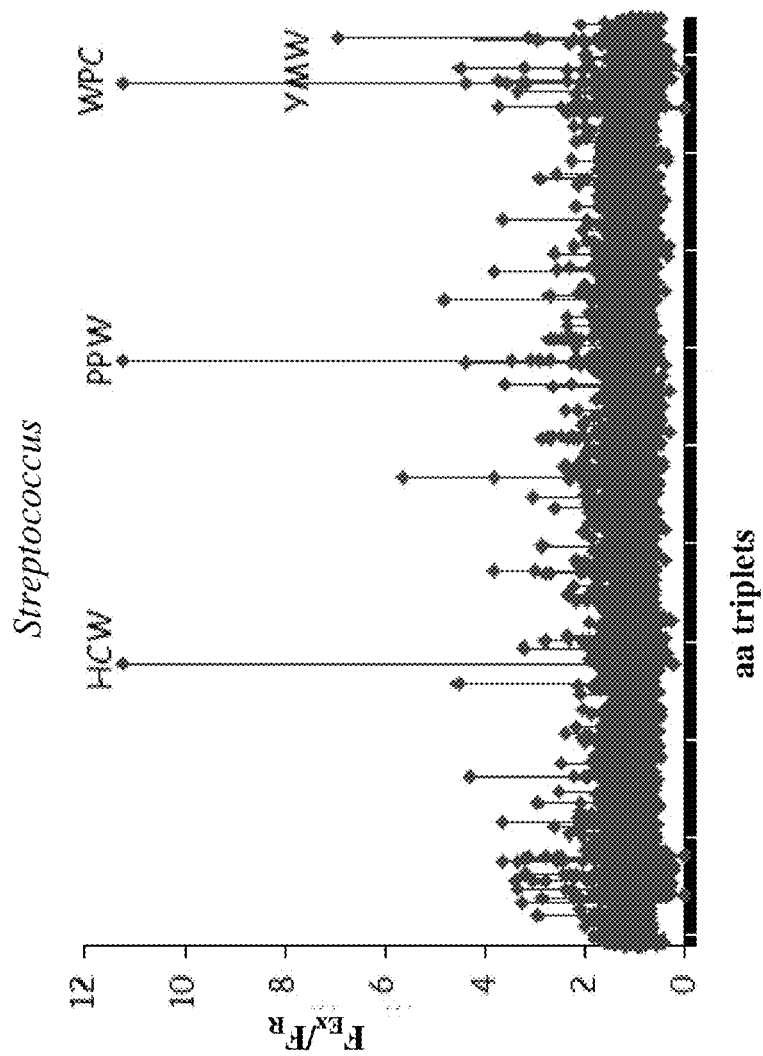
Figure 8G:
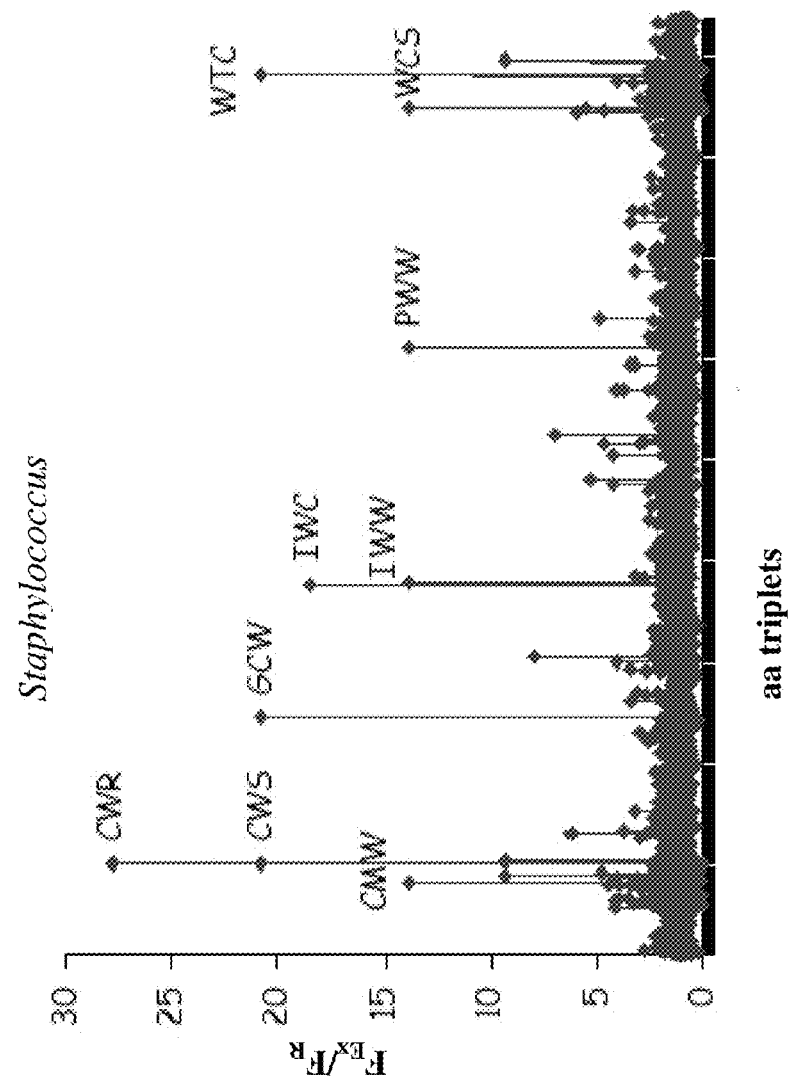
Figure 8H:
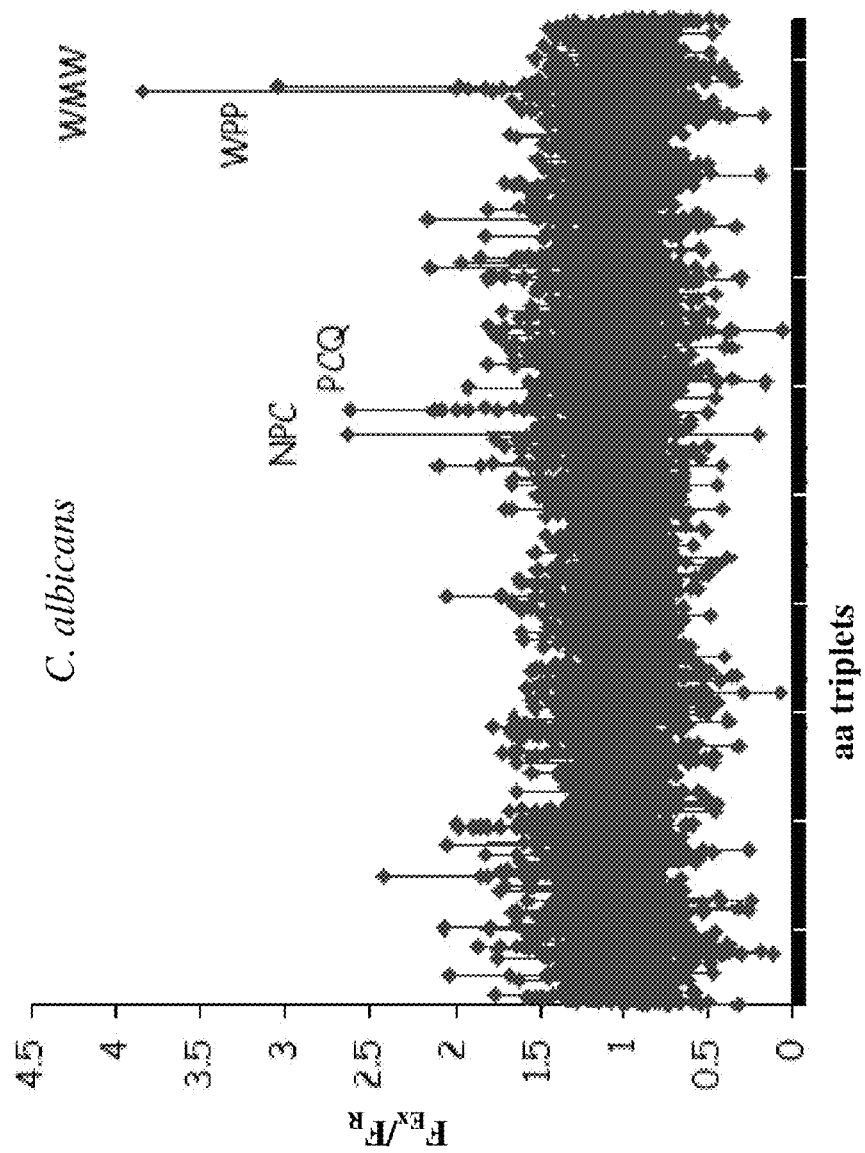
Figure 8I:
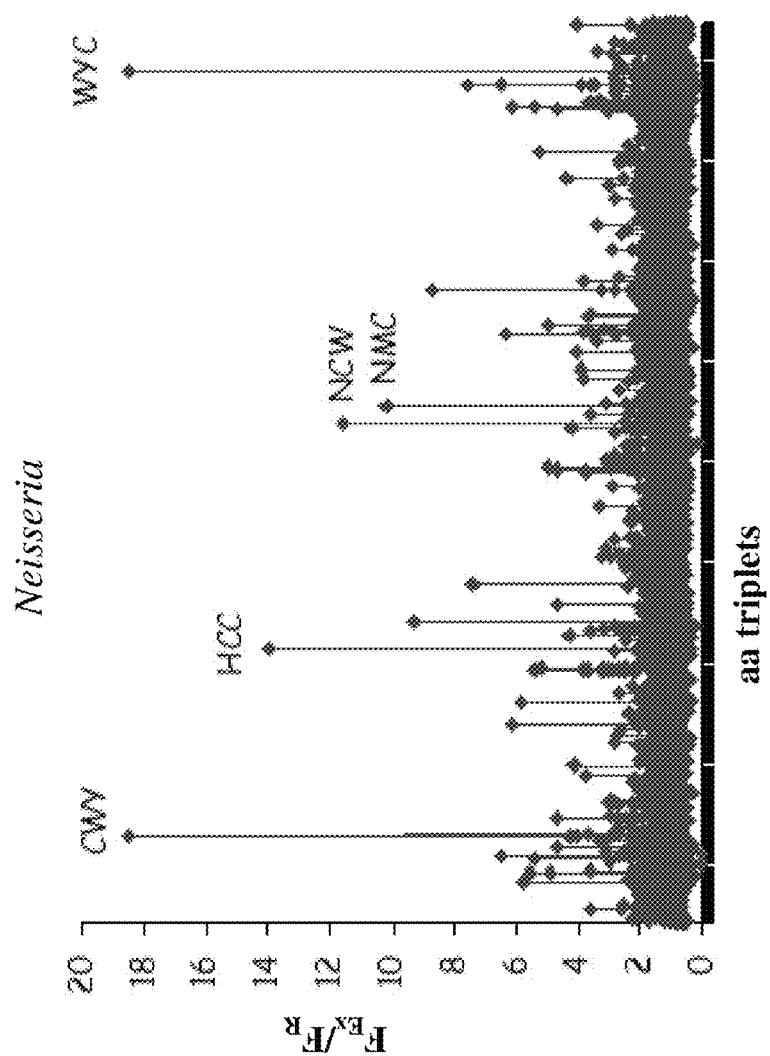
Figure 8J:
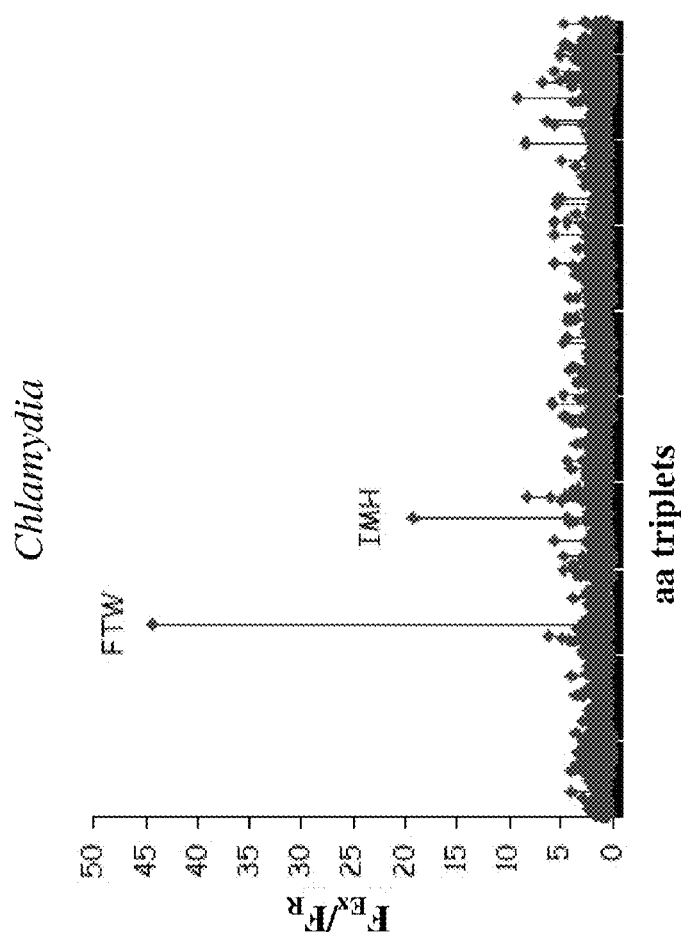
Figure 8K:
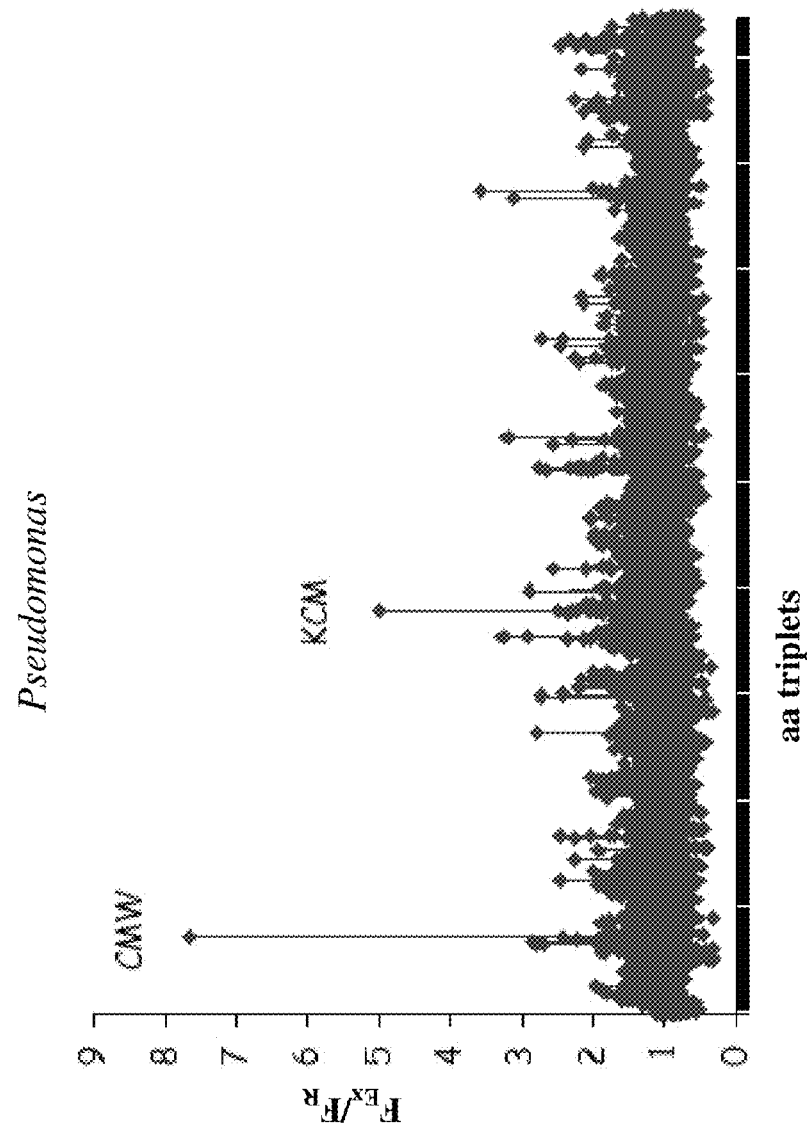
Figure 8L:
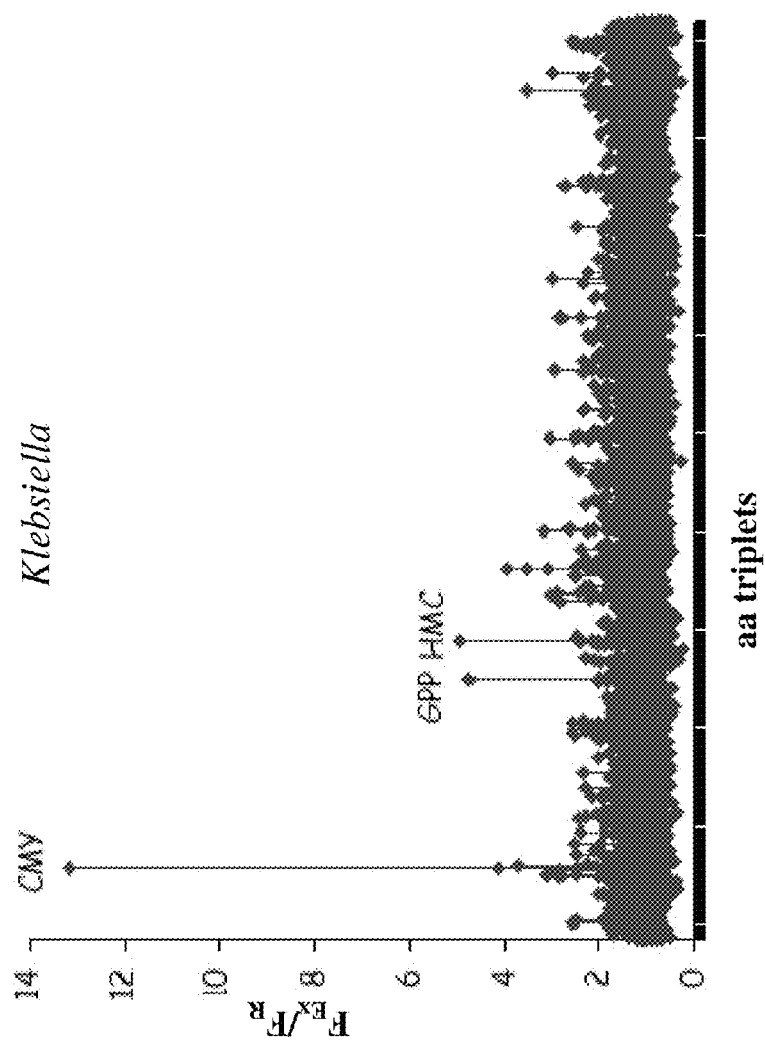
Figure 8M:
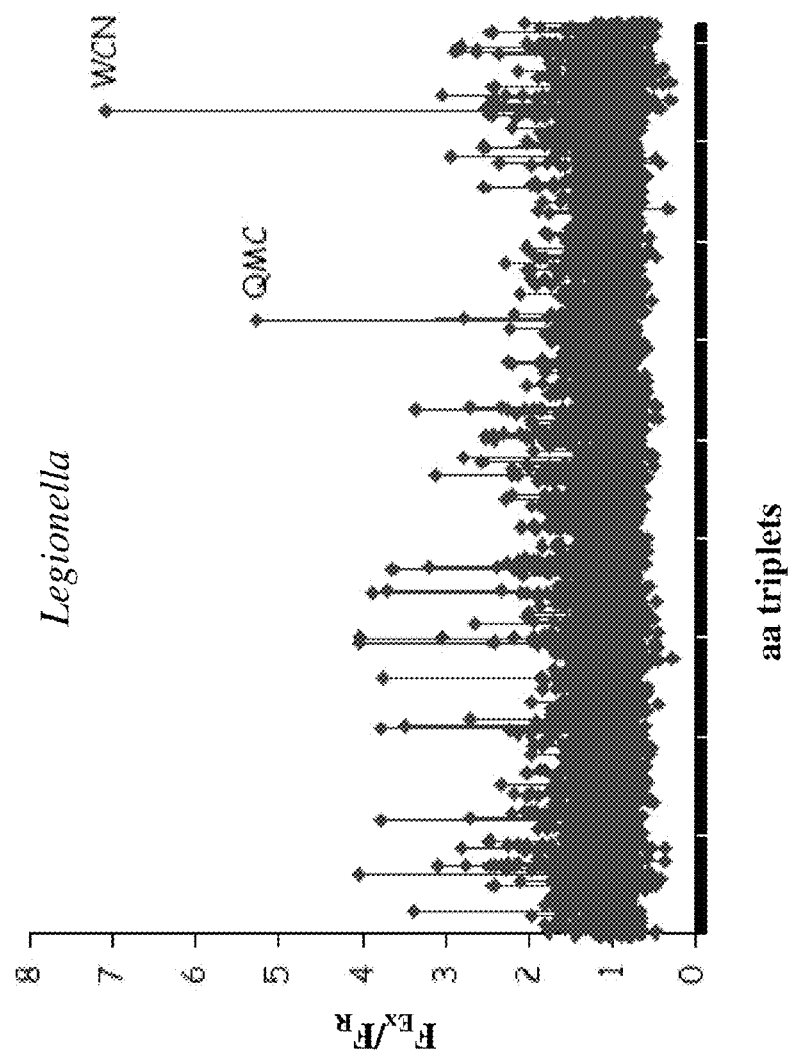
Figure 8N:
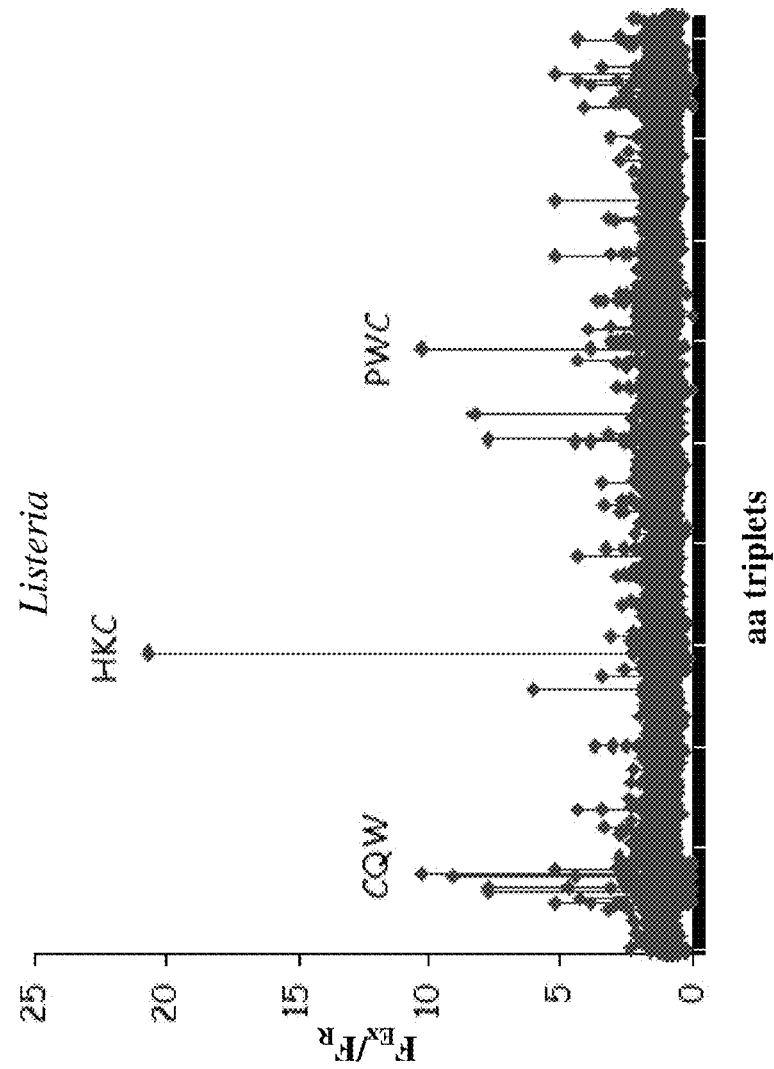
Figure 8O:
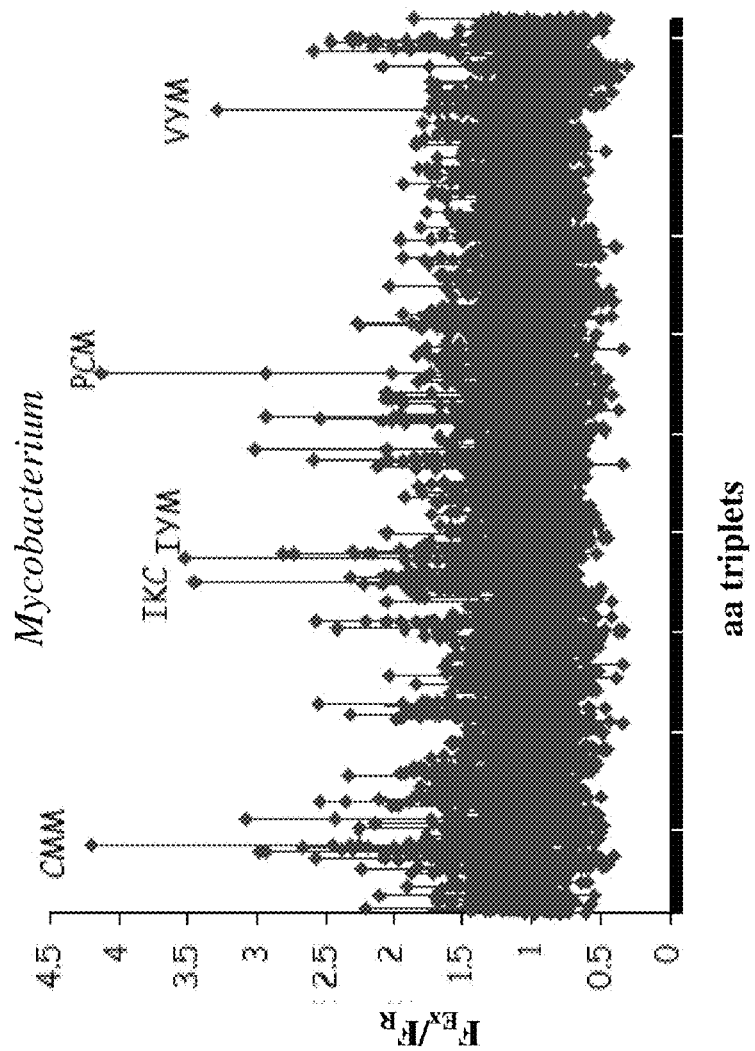
Figure 8P:
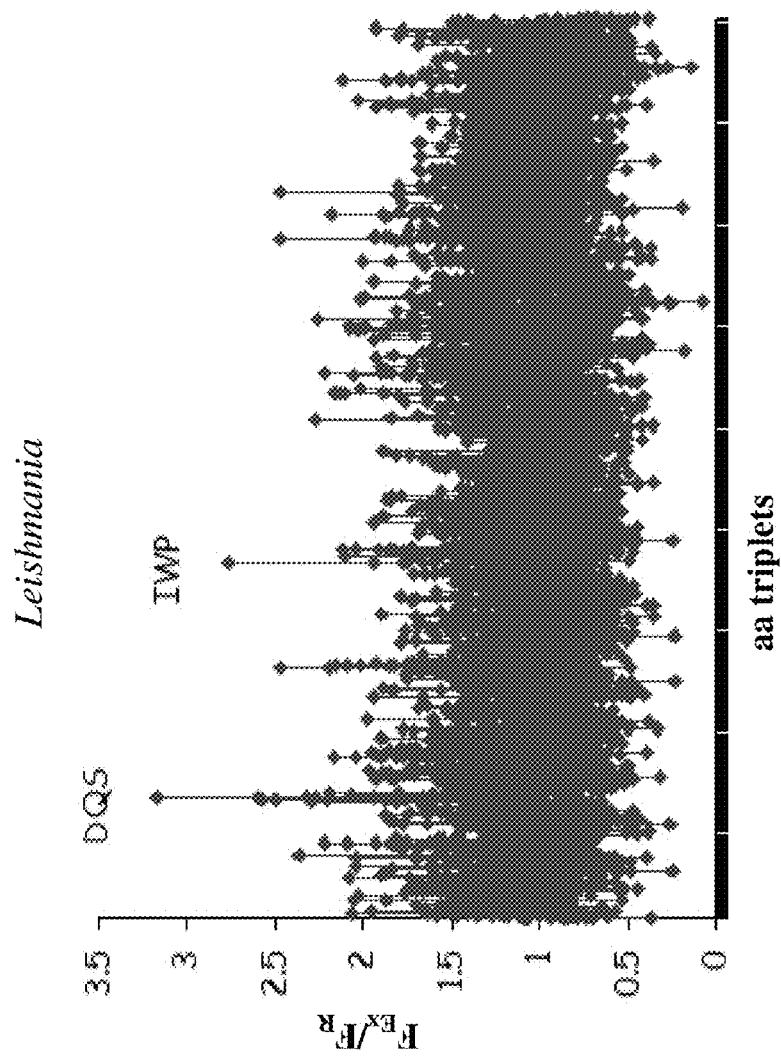
Figure 8Q:
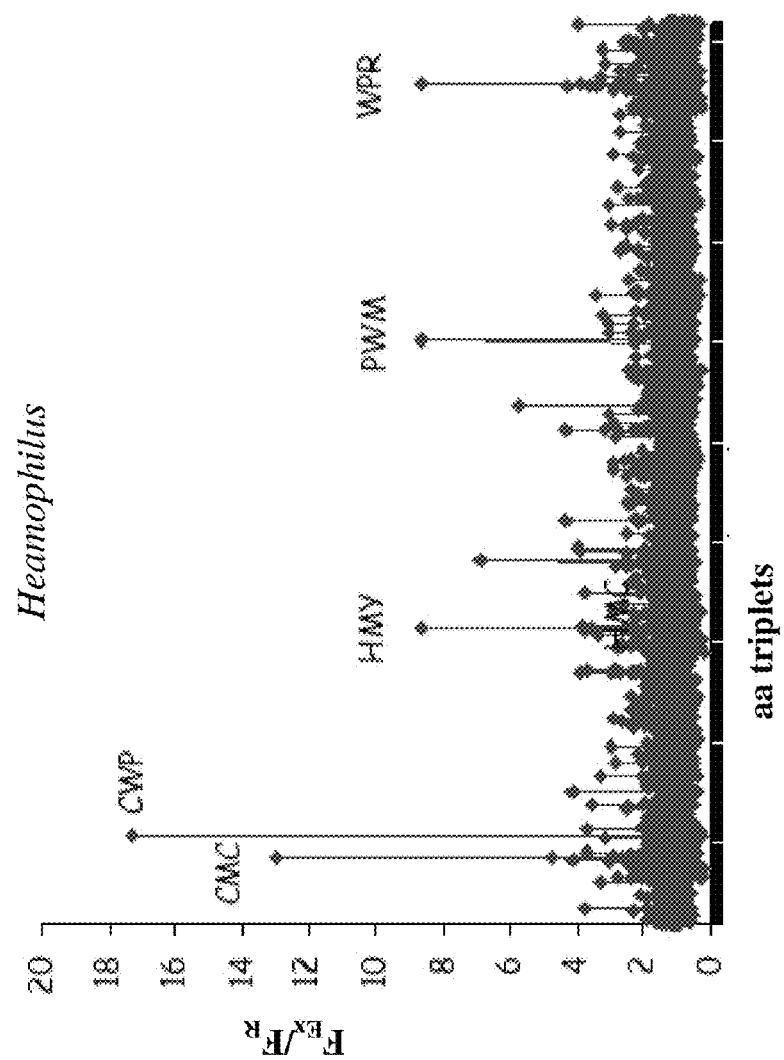
Figure 8R:
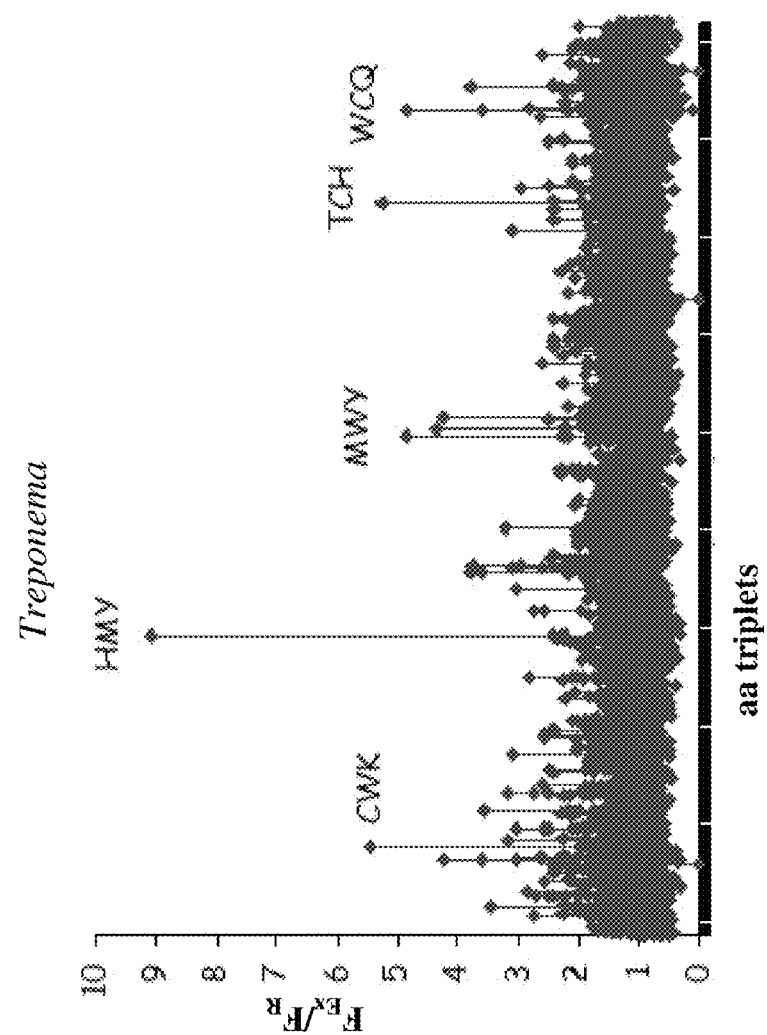
Figure 8S:
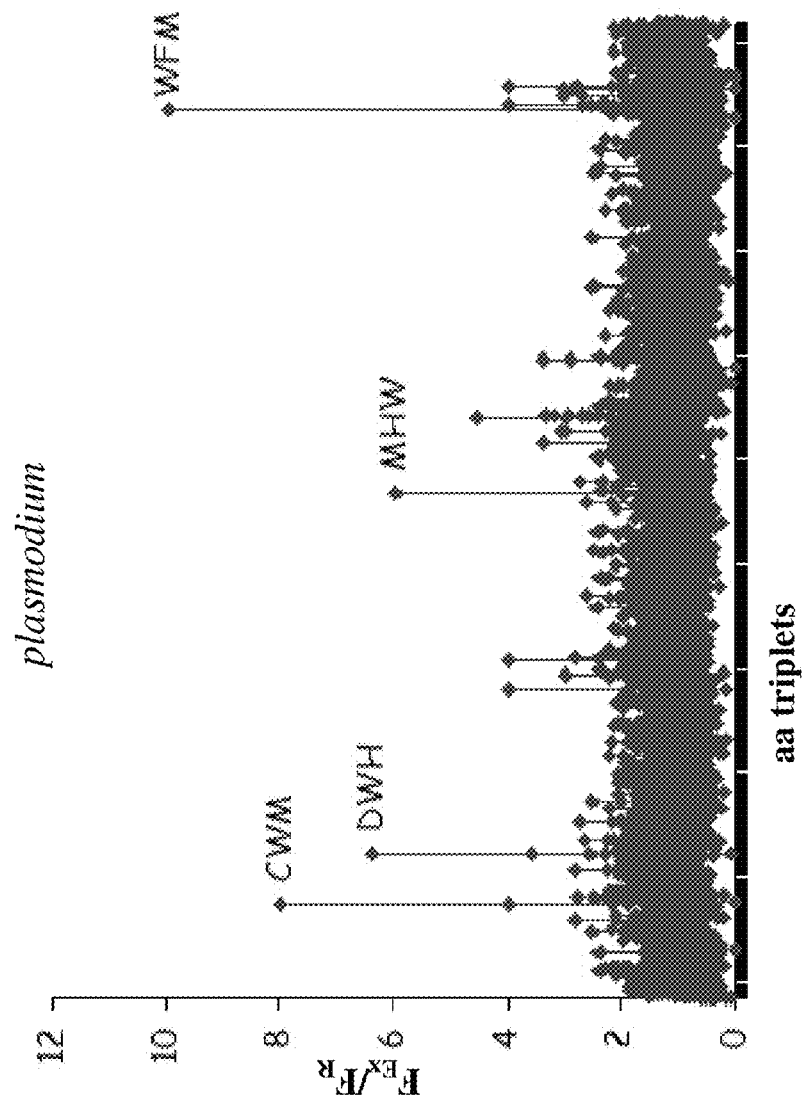
Figure 8T:
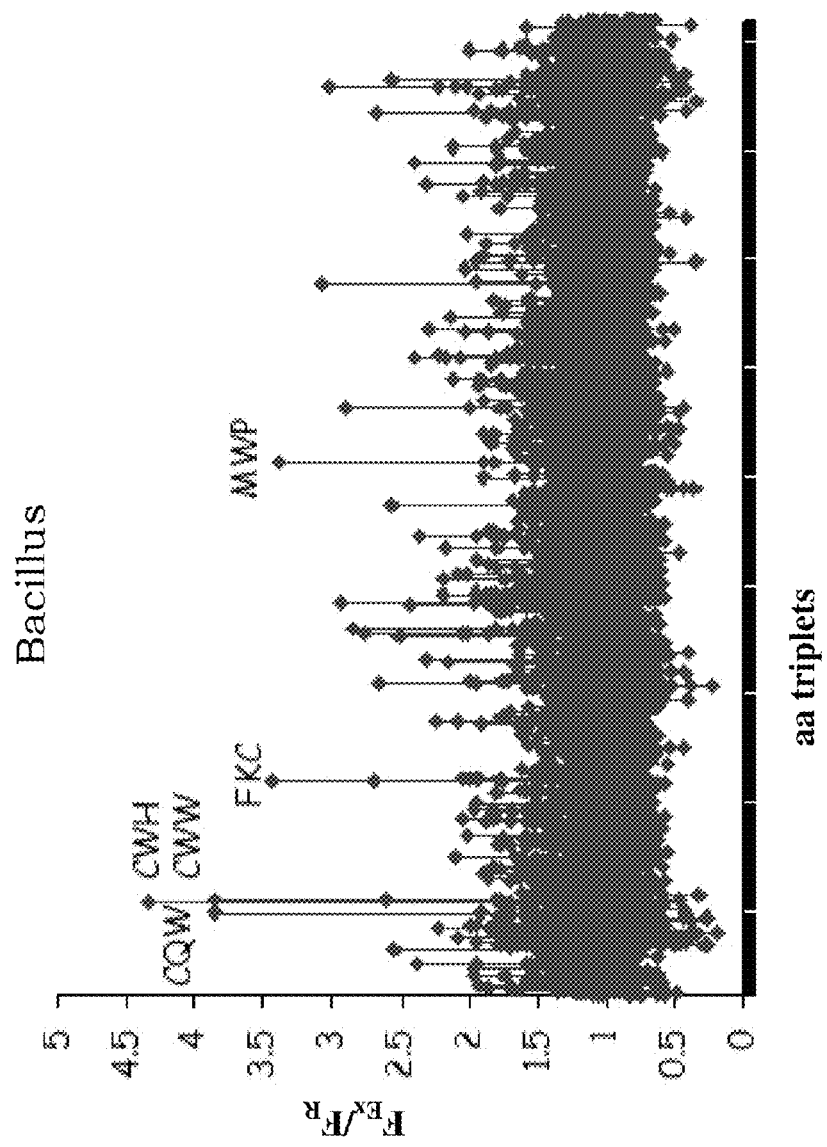
Figure 8U:
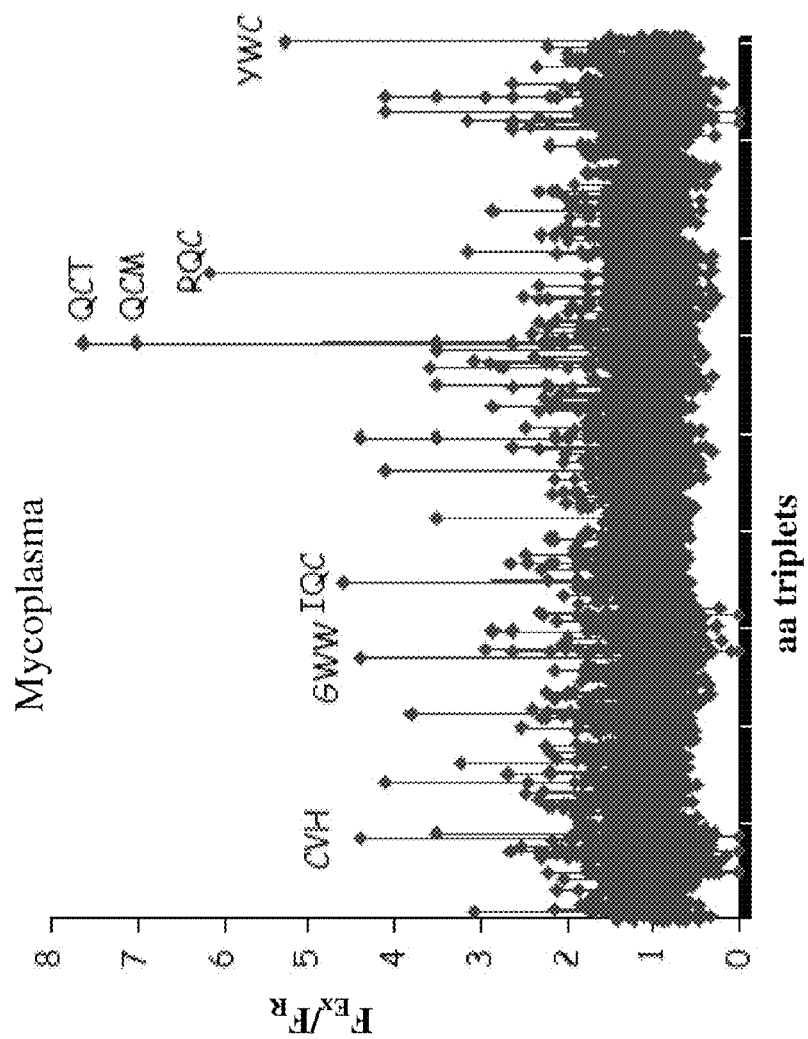
Figure 8V:
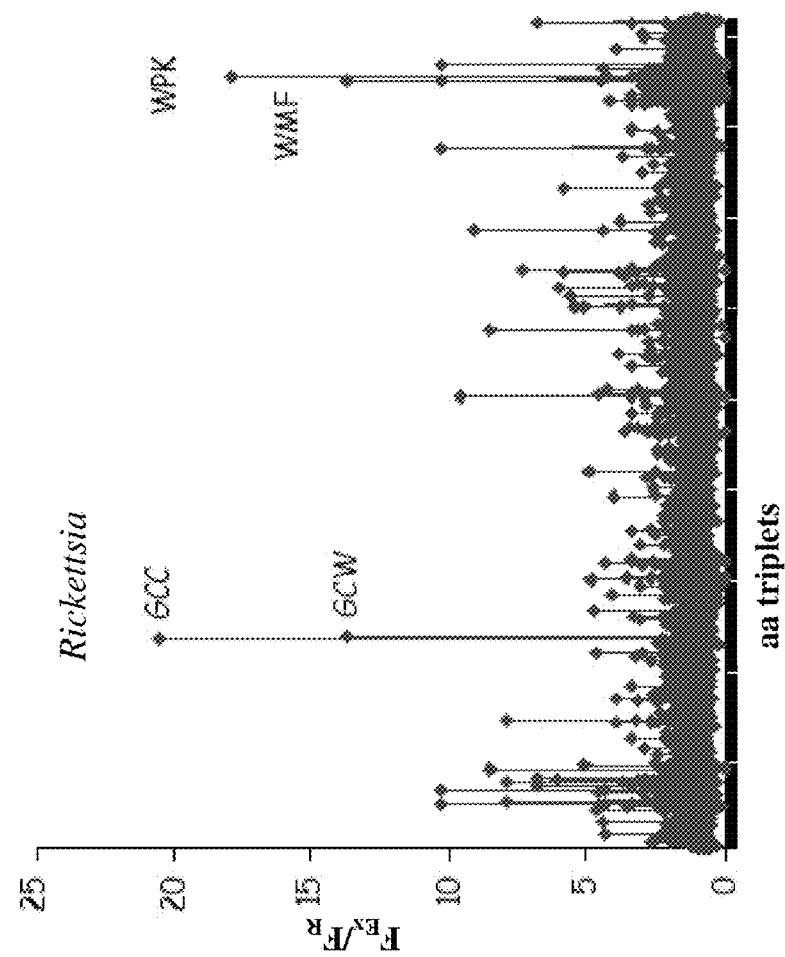
Figure 8W:
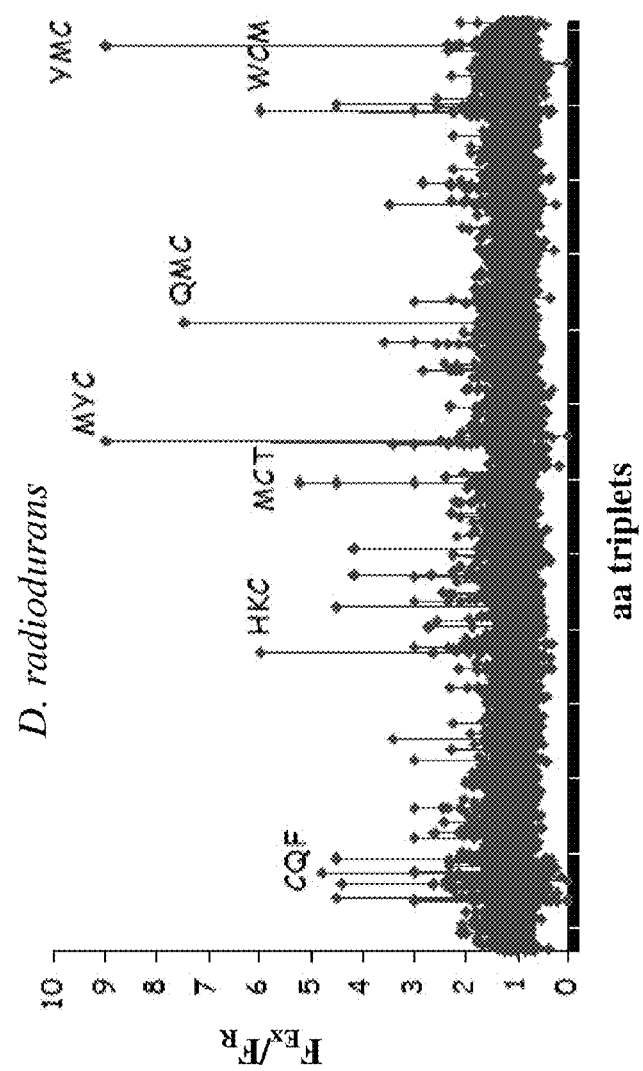
Figure 8X:
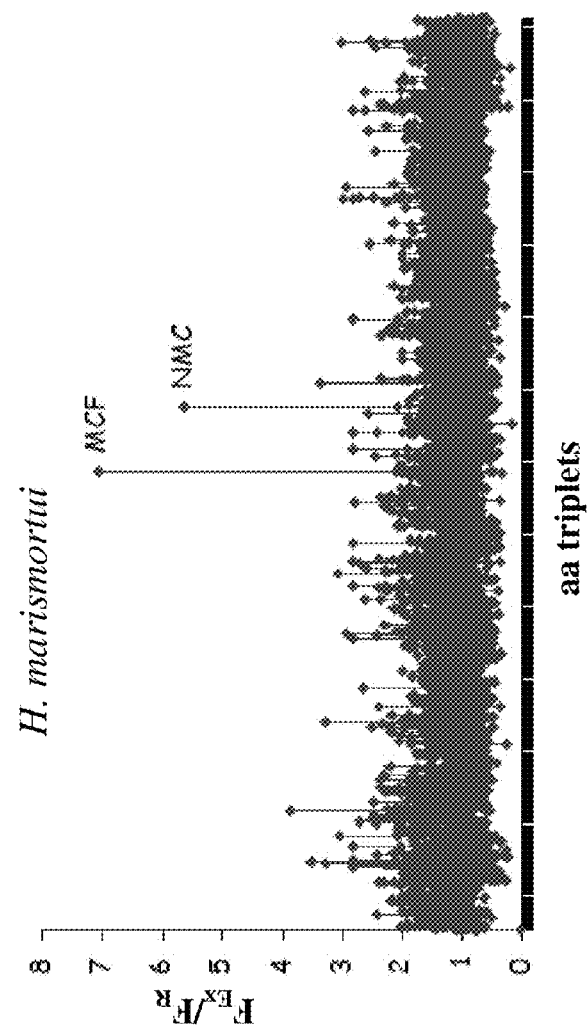
Figure 8Y:
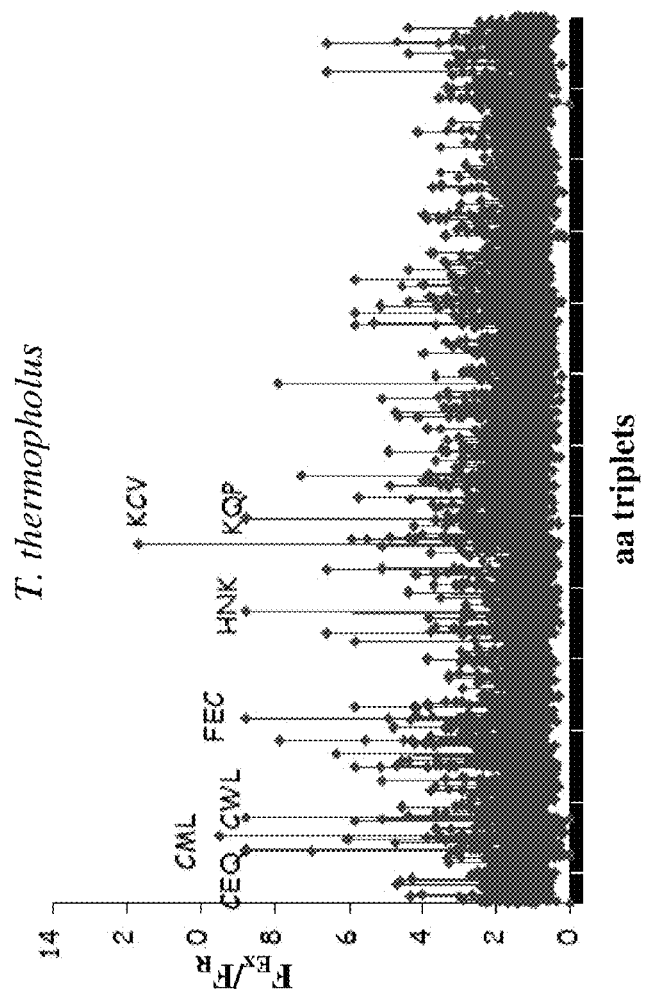

FIGS. 8A-Y are graphs illustrating URSs in a variety of pathogenic organism's (or genus's) proteomes. All the proteomic databases were downloaded from GIB-Genome Information Broker (world wide web gibdotgenesdotnigdotacdotjp), except for the *Candida* proteomes that downloaded from were NCBI (worldwidewebdotncbidotnlmdotnihdotgov). A, *Shigella* (7 proteomes); B, *Salmonella* (17 proteomes); C, *Campilobacter* (10 proteomes); D, *Vibrio* (12 proteomes); E, *Helicobacter* (9 proteomes); F, *Streptococcus* (44 proteomes); G, *Staphylococcus* (19 proteomes); H, *Candida* (3 proteomes); I, *Neisseria* (8 proteomes); J, *Chlamydia* (6 proteomes); K, *Pseudomonas* (17 proteomes); L, *Klebsiella* (3 proteomes); M, *Legionella* (4 proteomes); N, *Listeria* (4 proteomes); 0, *Mycobacterium* (22 proteomes); P, *Leishmenia* (1 proteome); Q, *Heamophilus* (8 proteomes); R, *Pseudomonas* (17 proteomes); S, *Plasmodium* (1 proteome); T, *Bacillus* (24 proteomes); U, *Mycoplasma* (5 proteomes); V, *Rickettsia* (13 proteomes); W, *D. radiodurans* (1 proteome); X, *H. marismortui* (1 proteome); Y, *T. thermopholus*, (1 proteome).

FIGS. 9A-B illustrates the positions of inserted URSs in target proteins. All the mutations were performed by QuikChange™ Site-Directed Mutagenesis Kit, Stratagene. A. T1-WT (MntA) amino acid sequence (SEQ ID NO: 1). The location of the URSs within the T1-WT sequence are marked: T1-1 (light purple) (SEQ ID NO: 33), T1-2 (magenta) (SEQ ID NO: 34), T1-3 (pink) (SEQ ID NO: 36) T1-4 (magenta' under lined) (SEQ ID NO: 35) and T1-5 (light blue) (SEQ ID NO: 3). B. T2-WT (GFP) amino acid sequence (SEQ ID NO: 2). The location of the URS and non-URS within the T2-WT sequence are marked in red (T2-1 and T2-2 (SEQ ID NOs: 37 and 38 respectively)).

Figure 10A:
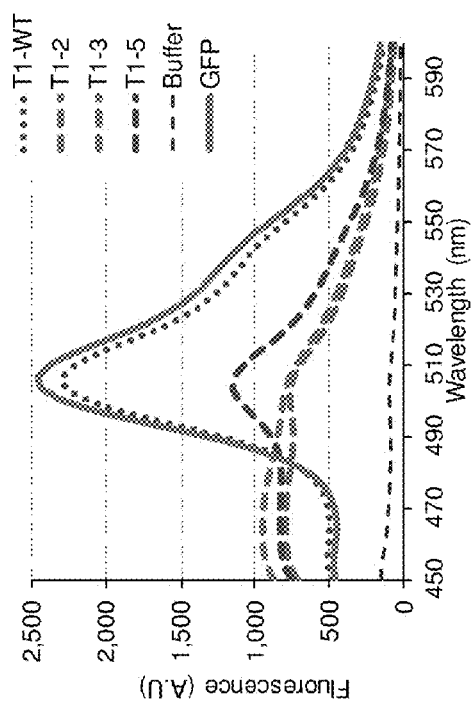
Figure 10B:
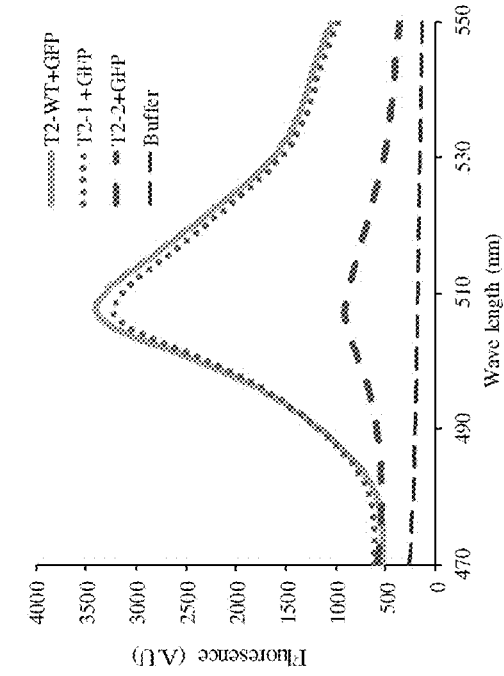

FIGS. 10A-B are graphs illustrating inhibition of translation of GFP in vitro by co-expression of URS mutants. The fluorescence of GFP obtained by in vitro translation performed during co-translation of target 1 (panel a) or target 2 (panel b) proteins. In vitro transcription/translation from plasmids expressing target 1 WT or mutants or target 2 mutants was performed for 20 min at 30° C., followed by the addition of the T2-WT (GFP) plasmid. The reactions were then further incubated for 4 hours at 30° C. GFP maturation was performed at 4° C. for 24 hours, followed by measurement of the GFP fluorescence using a MD SpectraMax Plus 384 Spectrophotometer with excitation at 395 nm and emission between 450 to 600 nm.

Figure 11:
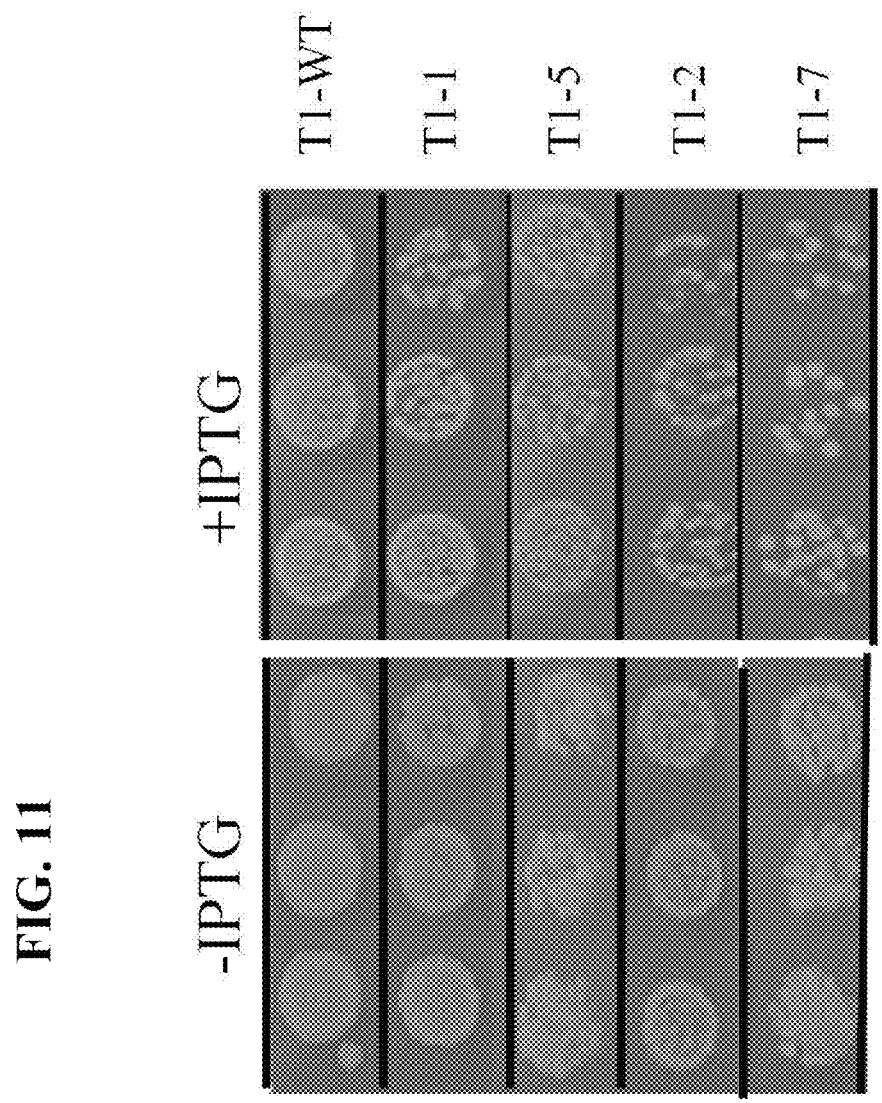

FIG. 11 illustrates that expression of proteins with embedded URSs compromises cell growth. Equal amounts of BL21 (DE3) pLysS *E. coli* cells containing T1-wt or T1 with embedded URSs were diluted with fresh LB for a series of ten-fold dilutions. 4 µl of each dilution were platted on fresh LBA (left) or LBA with 2 mM IPTG (right). Far fewer colonies are seen in the presence of IPTG when T1 URS mutations are expressed.

Figure 12:
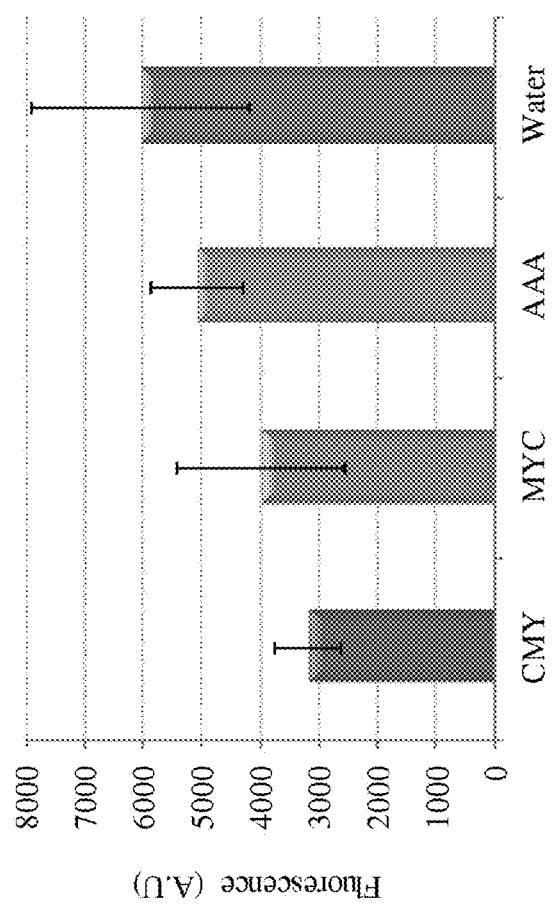

FIG. 12 is a graph illustrating in vitro inhibition of target 2-wt (GFP) expression in the presence of 0.01M synthetic tripeptides: AAA, MYC, CMY or in the absence of peptides. The fluorescence of GFP in each reaction was measured as described above.

FIGS. 13A-B illustrate potential areas of nascent protein-ribosomal tunnel interaction affected by URSs. A. Three polypeptides penetrate the 50S ribosomal subunit rRNA structure and extend into the exit tunnel. The structures of these proteins (L4, L22 and L23) have been determined by X-ray crystallography from four organisms: *D. radiodurans* (hotpink, PDB code 2ZJR), *T. thermophilus* (yellow, PDB code 3I8I), *H. marismortui* (green, PDB code 3CC2) and *E. coli* (marine, PDB code 2AW4). The loops of these proteins that penetrate into the tunnel were superimposed. The insert at right shows the positions of these three proteins in relation to the 23S rRNA (gray surface representation). B. The alignment of these protein sequences in the protruding loop domain (color) was performed using ClustalW (worldwidewebdotebidotacdotuk/Tools/es/cgi-bin/clustalw). Notice that the L23 protein of *H. marismorttui* does not penetrate into the tunnel.

FIGS. 14A-E illustrate that proteins with embedded *E. coli* URSs are expressed at normal levels in HeLa cells. FACS analysis 48 h after transfection of HeLa cells with plasmids expressing T3-wt and mutants. A. Control, no plasmid. B. T3-wt. C. T3-1, D. T3-2, E. T3-3. In each panel the results are divided into four quadrants showing the number of cells: upper left—non-fluorescent live cells; upper right—fluorescent live cells; lower left—non-fluorescent dead cells; lower right—fluorescent dead cells.

DESCRIPTION OF SPECIFIC EMBODIMENTS OF THE INVENTION

The present invention, in some embodiments thereof, relates to peptide agents comprising anti-microbial properties and to methods of treating diseases using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

One of the most critical and ubiquitous of all cellular functions is the translation machinery of the ribosome. During translation, the nascent peptide, that is formed at the peptidyl transferase center (FIG. 1), traverses through an extended tunnel leading out from the 50S ribosome subunit. The dimensions of the tunnel (~120 Å in length and 10-25 Å in diameter) have been experimentally determined in the crystalline state, and while there are probably fluctuations in diameter due to thermal motion and/or directed conformational changes, the peptide most likely traverses the tunnel in a fully or partially unfolded state. The tunnel of eubacterial ribosomes is mostly lined by ribonucleotides from the 23S rRNA but also has contributions from three ribosomal proteins (L4, L22 and L23). The nucleotides are positioned along the tunnel in a variety of orientations, exposing different functional groups to the tunnels interior. In addition to specific chemical traits, the overall electrostatic potential of the tunnel has been shown to be rather negative. Thus, the tunnel presents a variety of potential binding sites which could be of both chemical and geometric complimentary toward the growing peptide.

The present inventors conceived that it may be possible that certain linear, short sequences (3-5 aa) might impart affinity to the tunnel, thus arresting translation in a fashion that would be both immune to the effect of outside agents or the force of the action of the ribosome. The arrested ribosome might disassemble or could be rescued by translation releasing the mRNA, 30S and 50S subunits. However if the affinity of the peptide is high enough, these 50S subunits would not be available for further rounds of translation. If the concentration of mRNA encoding for a protein containing such a sequence is high enough, the overall rate of translation in the cell would diminish and cell viability would be compromised. If the damaging potential of such sequences was great enough, negative evolutionary pressure would lead to their absence from the proteome.

The present inventors deduced that using existing comprehensive proteomic data, it should be possible to identify such sequences by "reverse bioinformatics" (i.e. by screening for data lacking a large data set; FIG. 2).

Accordingly, the present inventors analyzed all identified open reading frames (ORFs) in the proteomes of 29 strains of *E. coli* for which genomes have been determined, annotated and deposited (European Bioinformatics Institute). Five triplets were found to be significantly reduced in frequency and can thus be considered under-represented sequences (URSs), with CMY appearing a factor of 7 times less often than expected (FIG. 5A). This form of analysis was also applied to the proteomes of wide range of pathogenic microorganisms (FIGS. 8A-V).

By mutating two target genes such that they encoded at least one under-represented sequence, the present inventors showed that they inhibited translation of the genes in which they were embedded (FIGS. 5B-E). In-vitro expression of such genes showed a decrease in translation of both the mutated and their corresponding non-mutated genes (FIGS. 10A-B). Concurrent with a decrease in expression, the present inventors also noted a decrease in viability of the cells (FIG. 11).

Finally, using an exemplary URS (CMY), the present inventors showed that the peptide itself could serve as an efficient inhibitor of translation (FIG. 12).

Thus, according to one aspect of the present invention there is provided an isolated anti-microbial peptide being no longer than 10 amino acids, wherein at least one of the amino acids of the 10 amino acids is selected from the group consisting of tryptophan, cysteine, proline and methionine.

The phrase "antimicrobial activity" as used herein, refers to an ability to suppress, control, inhibit or kill microorganisms, such as bacteria and archae. Thus for example the antimicrobial activity may comprise bactericidal or bacteriostatic activity, or both.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs.

According to one embodiment, the peptide is capable of blocking a ribosomal exit tunnel of a microorganism.

According to a preferred embodiment, the peptide is between 3-8 amino acids, 3-7 amino acids, 3-6 amino acids or between 3-5 amino acids.

According to a specific embodiment, the peptide is 3 amino acids.

According to another specific embodiment, the peptide is 4 amino acids.

According to another specific embodiment, the peptide is 5 amino acids.

The present inventors have found that there are certain amino acids (and amino acid sequences) that are highly represented amongst the identified peptides.

Thus, for example, the present inventors have found that cysteine, methioinine, proline and tryptophan are highly represented.

The peptides may be consist entirely of the amino acids cysteine, methioinine, proline and tryptophan, or may comprise additional amino acids, such as tyrosine, glutamine or glycine.

According to a particular embodiment, the peptide comprises both a cysteine residue and a methionine residue.

According to another particular embodiment, the peptide comprises both a cysteine residue and a tryptophan residue.

According to still another embodiment, the peptide comprises at least two cysteine residues, two tryptophan residues or two proline residues. The above mentioned residues may be adjacent to one another (i.e. attached to each other by a peptide bond) or may be separated by 1 or 2 additional amino acids.

Exemplary amino acid sequences comprised in the peptides of the present invention include, but are not limited to CMY, CMYW (SEQ ID NO: 39), GPP, MWC, PCQ, WMC, CKF, MCM, MWC, WKC, YMC, CMW, CMY, CKC, CKF, NMC, WCM, CKW, CCY, CQQ, CWM, MCP, MWT, QCW, WKC, DPP, FMC, CCQ, HWM, WYT, HCW, PPW, WPC, YMW, CMR, CWS, GCW, IWC, IWW, PWW, WTC, WCS, NPC, PCQ, WPP, WMW, CWY, HCC, NCW, NMC, WYC, FTW, IMH, KCM, CMY, HMC, QMC, CQW, HKC, PWC, CMM, IKC, IYM, PCM, VYM, CMC, CWP, HMY, PWM, WPR, CWK, HMY, MWY, TCH, WCQ, DWH, MHW, WFM, CQW, CWH, CWW, FKC, MWP, CBH, GWW, IQC, QCT, QCM, RQC, YWC, GCC, GCW, WMF, WPK, CQF, HKC, MCT, MYC, QMC, YMC, MCF, NMC, CEQ, CML, CWL, FEC, KCV, KQP, DQS, IWP and HNK.

The peptides of the present invention may display selectivity towards a particular microbe. Below is a list of amino acid sequences which may be comprised in the peptides of the present invention which may impart selectivity towards a particular bacterium:

*Escherichia coli* (*E. coli*)—CMY, CMYW (SEQ ID NO: 39), GPP, MWC, PCQ and WMC.

*Shigella*—CMY. CKF, GPP, MCM, MWC, WKC, YMC.

*Salmonella*—CMW, CMY, CKC, CKF, GPP, NMC, WCM.

*Campylobacter*—CKW, CCY, CQQ, CWM, MCP, MWT, QCW, WKC.

*Vibrio*—CKW, CMW, DPP, FMC, GPP.

*Helicobacter*—CCQ, HWM, WYT.

*Streptococcus*—HCW, PPW, WPC, YMW.

*Staphylococcus*—CMW, CMR, CWS, GCW, IWC, IWW, PWW, WTC, WCS.

*C. albicans*—NPC, PCQ, WPP, WMW.

*Neisseria*—CWY, HCC, NCW, NMC, WYC.

*Chlamydia*—FTW, IMH.

*Pseudomonas*—CMW, KCM.

*Klebsiella*—CMY, GPP, HMC.

*Legionella*—QMC, WCM.

*Listeria*—CQW, HKC, PWC.

*Mycobacterium*—CMM, IKC, IYM, PCM, VYM.

*Leishmenia*—DQS, IWP.

*Heamophilus*—CMC, CWP, HMY, PWM, WPR.

*Treponema*—CWK, HMY, MWY, TCH, WCQ.

*Plasmodium*—CWM, DWH, MHW, WFM.

*Bacillus*—CQW, CWH, CWW, FKC, MWP.

*Mycoplasma*—CBH, GWW, IQC, QCT, QCM, RQC, YWC.

*Rickettsia*—GCC, GCW, WMF, WPK.

*D. radiodurans*—CQF, HKC, MCT, MYC, QMC, WCM, YMC.

*H. marismortui*—MCF, NMC.

*T. thermopholus*—CEQ, CML, CWL, FEC, HNK, KCV, KQP.

The peptides of this aspect of the present may comprise modifications or additions which render the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthyleanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |

TABLE 1-continued

| Amino Acid | Three-Letter Abbreviation | One-letter Symbol |
|---|---|---|
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclo-pentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |

TABLE 2-continued

| Non-conventional amino acid | Code | Non-conventional amino acid | Code |
|---|---|---|---|
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentyl-alanine | Nmcpen |
| N-methylglycine | Nala | D-N-methylphenyl-alanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenyl-alanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval | L-N-methylhomophenyl-alanine | Nmhphe |
| | Nnbhm | | |
| N-(N-(2,2-diphenylethyl) carbamylmethyl-glycine | Nnbhm | N-(N-(3,3-diphenylpropyl) carbamyl-methyl(1)glycine | Nnbhe |
| 1-carboxy-1-(2,2-diphenyl ethylamino)cyclo-propane | Nmbc | | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-microbial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may be attached (either covalently or non-covalently) to a penetrating agent.

As used herein the phrase "penetrating agent" refers to an agent which enhances translocation of any of the attached peptide across a cell membrane.

According to one embodiment, the penetrating agent is a peptide and is attached to the antimicrobial peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Cell penetrating peptide (CPP) sequences may be used in order to enhance intracellular penetration. CPPs may include short and long versions of TAT (YGRKKRR—SEQ ID NO: 18 and YGRKKRRQRRR—SEQ ID NO: 19), PTD (RRQRR—SEQ ID NO: 20), pVEC and TP10. However, the disclosure is not so limited, and any suitable penetrating agent may be used, as known by those of skill in the art.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such as: improve uptake into bacterial cells; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to still another embodiment, the antimicrobial peptides of the present invention are attached to a bacterial targeting moiety. The targeting moiety may aid in uptake of the attached antimicrobial moiety into the bacteria.

According to one embodiment, the bacterial targeting moiety is a peptide targeting moiety (e.g. an antibacterial peptide). Preferably the peptide targeting moiety is no longer than 10 amino acids, and even more preferably no longer than 5 amino acids. The bacterial targeting moiety should be selected such that it does not harm the ability of the antimicrobial peptide to penetrate the ribosomal tunnel. Exemplary bacterial targeting moieties are disclosed in International Patent Application WO2010080819A1.

According to another embodiment, the antimicrobial peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The peptides of the invention may be linear or cyclic (cyclization may improve stability, or uptake into the microbe). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are well known in the art and the components of the system are commercially available.

Since the peptides of the present invention comprise anti-microbial properties they may be used to kill microbes.

Thus, according to another aspect of the present invention there is provided a method of killing a microbe, the method comprising contacting the microbe with the isolated peptides of the present invention.

The microbe may be a bacteria, a fungus, a parasite a protozoa and an archaea.

The microbe may be for example a gram-positive or gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

As used herein the term "contacting" refers to the positioning of the peptides of the present invention such that they are in direct or indirect contact with the bacterial cells. Thus, the present invention contemplates both applying the peptides of the present invention to a desirable surface and/or directly to the bacterial cells.

Contacting surfaces with the peptides can be effected using any method known in the art including spraying, spreading, wetting, immersing, dipping, painting, ultrasonic welding, welding, bonding or adhering. The peptides of the present invention may be attached as monolayers or multiple layers.

The present invention envisages coating a wide variety of surfaces with the peptides of the present invention including fabrics, fibers, foams, films, concretes, masonries, glass, metals, plastics, polymers, and like.

An exemplary solid surface that may be coated with the peptides of the present invention is an intracorporial or extra-corporial medical device or implant.

An "implant" as used herein refers to any object intended for placement in a human body that is not a living tissue. The implant may be temporary or permanent. Implants include naturally derived objects that have been processed so that their living tissues have been devitalized. As an example, bone grafts can be processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components.

Thus, for example, the present invention therefore envisions coating vascular stents with the peptides of the present invention. Another possible application of the peptides of the present invention is the coating of surfaces found in the medical and dental environment.

Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; blood filters, implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Other surfaces related to health include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Examples can include food processing equipment for home use, materials for infant care, tampons and toilet bowls.

According to another embodiment the surface is comprised in a biological tissue, such as for example, mammalian tissues e.g. the skin.

It will be appreciated that the microbes may be comprised inside a particular organism, (e.g. intracellularly or extracellularly) for example inside a mammalian body or inside a plant. In this case, the contacting may be effected by administering the peptides per se or by transfecting the cells of the organism with a nucleic acid construct which comprises a nucleic acid sequence which encodes the peptides of the present invention.

Such a nucleic acid construct includes a promoter sequence for directing transcription of the polynucleotide sequence in the cell in a constitutive or inducible manner.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804) or pathogen-inducible promoters. Such promoters include those from pathogenesis-related proteins (PR proteins), which are induced following infection by a pathogen.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof. The nucleic acid construct of some embodiments of the invention may also include a signal sequence.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl.

Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of the antimicrobial peptides of the invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Where appropriate, the polynucleotides may be optimized for increased expression in the transformed organism. For example, the polynucleotides can be synthesized using preferred codons for improved expression. For optimal expression in plants or fungi, the pre- and propeptide sequences may be needed. The propeptide segments may play a role in aiding correct peptide folding.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as beta-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP™ from Evrogen, see, Bolte et al. (2004) J. Cell Science 117:943-54). The above list of selectable marker genes is not meant to be limiting. Any selectable marker gene can be used in the present invention.

As mentioned, one type of organism which may be transfected with expression constructs encoding peptides of the present invention is a plant.

Thus, the present invention contemplates, a plant, transformed by the antimicrobial RNA or peptides of the present invention (or an offspring thereof) rendered resistant to a plant-pathogenic microorganism. The plant (or plant cells thereof) are transformed with a nucleic acid construct comprising a nucleic acid sequence which encodes an antimicrobial gene product (RNA or peptide) of the present invention located under the control of a suitable promoter capable of functioning in plant cells. The transformed plant of the present invention can express, in its body, the protein having an antimicrobial activity according to the present invention.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp.,

*Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

The expression vector usable in the method of transforming plant cells with the gene of the present invention include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also be used. The terminator gene to be ligated may include a 35S terminator gene and a Nos terminator gene.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

Since the peptides of the present invention have antimicrobial activity, the present invention contemplates use thereof for treating infection in a mammalian subject.

According to one embodiment, the peptides are used to treat a topical infection (i.e. infection of the skin) and are provided in a topical formulation.

According to another embodiment, the peptides are used to treat an infection inside the body. In this case, the peptides (or polynucleotides encoding same) may be provided ex vivo or in vivo.

Accordingly, the present invention contemplates contacting cells with the peptides (or with expression constructs that encode the peptides) per se or as part of a pharmaceutical composition.

The pharmaceutical compositions of the present invention are administered to a subject in need thereof in order to prevent or treat a bacterial infection.

As used herein, the term "subject in need thereof" refers to a mammal, preferably a human subject.

As used herein, the term "treating" refers to curing, reversing, attenuating, alleviating, minimizing, suppressing or halting the deleterious effects of a pathogen infection.

The phrase "pharmaceutical composition", as used herein refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to peptides of the present invention accountable for the intended biological effect. It will be appreciated that a polynucleotide encoding a peptide of the present invention may be administered directly into a subject (as is, or part of a pharmaceutical composition) where it is translated in the target cells i.e. by gene therapy. Accordingly, the phrase "active ingredient" also includes such polynucleotides.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference and are further described herein below.

It will be appreciated that the peptides of the present invention can be provided to the individual with additional active agents to achieve an improved therapeutic effect as compared to treatment with each agent by itself.

Exemplary additional agents include antibiotics (e.g. rifampicin, chloramphenicol and spectinomycin).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The preparation of the present invention may also be formulated as a topical compositions, such as a spray, a cream, a mouthwash, a wipe, a foam, a soap, an oil, a solution, a lotion, an ointment, a paste and a gel.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, the presently disclosed peptides were uncovered based on their frequency of occurrence in the proteome of the microorganism.

Thus, according to another aspect of the present invention there is provided a method of synthesizing an anti-microbial agent, the method comprising:

(a) determining a frequency of a 3-5 amino acid sequence in an open reading frame (ORF) of a proteome of a microbe to obtain an actual frequency of the sequence;

(b) multiplying a frequency of each individual amino acid of the 3-5 amino acid sequence in the ORF of the proteome of the microbe to obtain an expected frequency of the sequence;

(c) comparing the actual frequency with the expected frequency, wherein at least a two fold (more preferably at least a four fold) reduction in the actual frequency compared to the expected frequency is indicative of a sequence of an antimicrobial agent; and (d) synthesizing the antimicrobial agent selected in step (c), thereby synthesizing the antimicrobial agent.

Synthesizing the peptide may be effected using any method including those detailed herein above.

Following synthesis the peptide may be tested for anti-microbial activity on any number of pathogenic and/or non-pathogenic organisms to determine the spectrum of activity. For example, the peptides may be tested on various bacteria to determine whether they have a bactericidal or bacteristatic effect. Minimal inhibitory concentration (MIC) can be determined by testing the growth inhibition activity of serial dilutions of the peptide.

To test if the peptides inhibit microbe growth when introduced from inside the cell, selected genes can be cloned into a vector that contains a tightly regulated inducible promoter, such that the expression of the gene is induced only after a specific molecule ("inducer") was added to the growth media. Such vectors could be inserted into *E. coli* without killing it, as the gene product will only be expressed in the cell following induction. Growth of *E. coli* can be tested before and after induction to determine if the gene has a growth inhibition effect.

Additionally, in vitro antimicrobial assays that can be used include, for example, the addition of varying concentrations of the antimicrobial composition to paper disks and placing the disks on agar containing a suspension of the pathogen of interest. Following incubation, clear inhibition zones develop around the discs that contain an effective concentration of the antimicrobial polypeptide (Liu et al. (1994) Plant Biology 91:1888-1892, herein incorporated by reference). Additionally, microspectrophotometrical analysis can be used to measure the in vitro antimicrobial properties of a composition (Hu et al. (1997) Plant Mol. Biol. 34:949-959 and Cammue et al. (1992) J. Biol. Chem. 267: 2228-2233, both of which are herein incorporated by reference). Assays that specifically measure antibacterial activity are also well known in the art. See, for example, Clinical and Laboratory Standards Institute, Guideline M7-A6, Methods for dilution antimicrobial susceptibility tests for bacteria that grow aerobically, herein incorporated by reference.

Once antimicrobial activity has been confirmed, larger amounts (e.g. commercial quantities) of the peptide may be synthesized.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Bioinformatics:

The computational methodology whereby URSs or ORSs were identified, are shown in FIG. 2.

Embedding Under-Represented Sequences (URSs) into Target Proteins:

URSs were embedded into different segments of two genes. Target 1—the *Synechocystis* sp. PCC 6803 mntA gene (Gene Bank code AAA68931.1.) was cloned into a pET 20b+ expression vector which adds a 6xHis tag on the proteins C-terminal. Target 2 was obtained by expression of the gfp (*Aequorea victoria*; gene bank code AAA27721) gene cloned into the pIVEX2.3-GFP plasmid (Roche). Mutagenesis was executed by use of the QuickChange Site-directed mutagenesis kit (Stratagene), and confirmed by restriction enzyme fragment analysis (FIGS. 3A-B) and by sequencing (FIGS. 4A-F). All of the constructs containing the WT or a mutated mntA gene were transformed into BL21 (DE3) pLysS *E. coli* expression strain.

The primers used for site-specific mutagenesis of the target genes are presented in Table 1 herein below (in T1-1, both F and R are marked). The mutation sites are marked in bold and underlined.

TABLE 1

| Mutant name | Primer name | Primer sequence |
|---|---|---|
| T1-1 | CMY1F SEQ ID NO: 4 | 5'- GCAGCCACCCTATCTCGTCTTGA TATATGCATGTATGGTGTCAGCGTTA-3' |
|  | CMY1R SEQ ID NO: 5 | 5'- TAACGCTGACACCATACATGCATA TATCAAGACGAGATAGGGTGGCTGC-3' |
| T1-2 | CMY2F SEQ ID NO: 6 | 5'- GATATATCCGTCGATGGTGTCAGC TGCATGTATAACAACGCCCGTTTGGCCCTT-3' |
|  | CMY2R SEQ ID NO: 7 | 5'-AAGGGCCAAACGGGCGTTGTTATACAT GCAGCTGACACCATCGACGGATATATC-3' |
| T1-3 | CMY3F SEQ ID NO: 8 | 5'-GTTTGATGTGGTGATGATGGGGCGC TGCATGTATATGAATGTGTTGCGTATTCCTAG-3' |
|  | CMY3R SEQ ID NO: 9 | 5'-CTAGGAATACGCAACACATTCATATA CATGCAGCGCCCCATCATCACCACATCAAAC-3' |
| T1-4 | MWCF SEQ ID NO: 10 | 5'-TCCGGCGGTCAAAAGAAGCGGGCATTTT TGATGTGGTGTTTGGCCCAGGAAGGCAAGG-3' |
|  | MWCR SEQ ID NO: 11 | 5'-CCTTGCCTTCCTGGGCCAAACACCACATC AAAAATGCCCGCTTCTTTTGACCGCCGGA-3' |
| T1-2W | CMYW2 SEQ ID NO: 12 | 5'-TGATTTGGCCTCCATTTCCACCTTTTGT ATGTATACAATTCTGCTCAACCGCACTATTTTGGCCC-3' |
|  | CMYW2 SEQ ID NO: 13 | 5'-GGGCCAAAATAGTGCGGTTGAGCAGAAT TGTATACATACAAAAGGTGGAAATGGAGGCCAAATCA-3' |
| T2-1 | GCMYF SEQ ID NO: 14 | 5'-TGAAGAACTTTTCACTGGAGTTGTCTGCATGTAT GTTGAATTAGATGGTGATGTTAATGGGCACAAA-3' |
|  | GCMY SEQ ID NO: 15 | 5'- TTTGTGCCCATTAACATCACCATCTAATTCAA CATACATGCAGACAACTCCAGTGAAAAGTTCTTCA -3' |
| T2-2 | GMYCF SEQ ID NO: 16 | 5'- TGAAGAACTTTTCACTGGAGTTGTC ATGTATTGTGTTGAATTAGATGGTG ATGTTAATGGGCACAAATTTTC -3' |
|  | GMYCR SEQ ID NO: 17 | 5'- GAAAATTTGTGCCCATTAACATCACC ATCTAATTCAACACAATACATGACAACTC CAGTGAAAAGTTCTTCA -3' |

Quantification of the Effect of URSs on In Vitro Translation:

In vitro cell-free transcription/translation was performed using the RTS 100 *E. coli* HY Kit (Roche). The internal control of the commercial kit is a plasmid that expresses the fluorescent protein, GFP. This control was used to assess the effect of co expression with the target 1 mntA gene (WT or URS embedded mutants) or the target 2 (mutated GFP) in the presence of WT GFP. The effect of synthetic tripeptides (AAA, CMY and MYC) was performed in a similar manner.

Peptides (GL Biochem Ltd., Shanghai, China) were solubilized in DDW and added to the transcription/translation solution to a final concentration of 0.01M. The amount of GFP produced by the in vitro reaction was analyzed by fluorescence measurement as described above.

Quantification of the Effect of URSs on Translation and Cell Viability:

Evaluation of bacterial growth on liquid media was performed by measuring the optical density at 600 nm (OD600). A bacterial solution with an OD600 of 1 has a concentration of ~8×10$^8$ cells/ml. The influence of the URSs presence was evaluated by spectroscopic measurements of optical density (in comparison with the wild type) at different time intervals while maintaining the same growth conditions. The level of mutated protein expression was examined by SDS-PAGE after inducing the expression using isopropyl-β-D-thiogalactopyranoside (IPTG). IB band intensities were digitally measured using GelAnalyser2010.

Example 1

Identification of Under-Represented Sequences

All identified open reading frames (ORFs) in the proteomes of 29 strains of E. coli for which genomes have been determined, annotated and deposited (European Bioinformatics Institute) were analyzed (using the EMBL-EBI data base). The ratio between the expected appearance probability and the actual frequency of appearance of all of the 8000 possible aa triplets was calculated, which identified significant under represented sequences (URSs) or over represented sequences (ORSs). FIG. 5A shows a reverse expectancy plot that identifies possible triplet URSs. The ratio between the expected number of appearances ($N_{ex}$) of each aa triplet based on the product of frequencies of each aa within the proteome) to actual number of appearances ($N_r$) was plotted for all 8.33×10$^7$ aa triplets found in all 29 proteomes. Almost all triplets appear at near the expected ratio of 1, i.e. they appear nearly the same number of times as expected. Five triplets are significantly reduced in frequency and can thus be considered URSs, with CMY appearing a factor of 7 times less often than expected. The other permutations of these three residues (YMC, MCY, etc.) occur at nearly the expected number of times, indicating that the lack of a certain sequence is not just a result of the reduced usage of Cys and or Met. In fact, Cys, Tyr, Trp and Met also appear in sequences that are more highly represented than expected (FIG. 6). Further analysis showed that there are more than 5000 quadruplet which do not appear in the database at all. Interestingly, although the ribosome tunnel has been proposed to be significantly negatively charged, the potentially highly positively charged quadruplets (KKKK (SEQ ID NO: 40), RRRR (SEQ ID NO: 41)) are not URSs. A similar analysis of the human proteome revealed the presence of URSs, however they are different than those identified in E. coli (FIG. 7). This form of analysis was also applied to the proteomes of wide range of pathogenic microorganisms (FIGS. 8A-Y), showing that related species tend to have the similar URSs, while non-related species have other URSs. This observation is consistent with structural changes that may be manifested by the differences in the level of homology in the sequences of the ribosomal proteins that penetrate into the exit tunnel, and by differences in the rRNA residues that line the tunnel.

Example 2

Effect of URSs on Protein Expression

Having proved that the E. coli proteome indeed contains URSs, the present inventors wished to ascertain whether the presence of a URS in a nascent protein has the ability to affect translation. The most statistically significant URS in E. coli (CMY and MWC) were embedded by site directed mutagenesis into two cloned target genes (see Methods). Target 1 (NP_441238.1, MntA) was cloned into two IPTG inducible vector and the CMY URSs were embedded at three different locations along the gene identified as T1-1, T1-2 and T1-3 (FIG. 9A and Table 2, herein below).

TABLE 2

| Mutant Name | Protein | Position | URS | Expression Vectors |
| --- | --- | --- | --- | --- |
| T1-WT | MntA | — | — | pET 20b$^+$, pET 45b$^+$ |
| T1-1 | MntA | 1 | CMY | pET 20b$^+$, pET 45b$^+$ |
| T1-2 | MntA | 2 | CMY | pET 20b$^+$, pET 45b$^+$ |
| T1-3 | MntA | 3 | CMY | pET 20b$^+$, pET 45b$^+$ |
| T1-4 | MntA | 1 | WCMY (SEQ ID NO: 42) | pET 20b$^+$, pET 45b$^+$ |
| T1-5 | MntA | 1 | CMYW (SEQ ID NO: 39) | pET 20b$^+$, pET 45b$^+$ |
| T1-6 | MntA | 2 | WCMY (SEQ ID NO: 42) | pET 20b$^+$, pET 45b$^+$ |
| T1-7 | MntA | 2 | CMYW (SEQ ID NO: 39) | pET 20b$^+$, pET 45b$^+$ |
| T1-8 | MntA | 3 | WCMY (SEQ ID NO: 42) | pET 20b$^+$, pET 45b$^+$ |
| T1-9 | MntA | 3 | CMYW (SEQ ID NO: 39) | pET 20b$^+$, pET 45b$^+$ |
| T1-10 | MntA | 4 | MWC | pET 20b$^+$, pET 45b$^+$ |
| T2-WT | GFP | — | — | pIVEX2.3-GFP, pET 45b$^+$ |
| T2-1 | GFP | 1 | CMY | pIVEX2.3-GFP, pET 45b$^+$ |
| T2-2 | GFP | 1 | MYC | pIVEX2.3-GFP, pET 45b$^+$ |
| T2-3 | GFP | 1 | CMYW (SEQ ID NO: 39) | pIVEX2.3-GFP, pET 45b$^+$ |
| T3-WT | EGFP | — | — | EGFP-N1 |
| T3-1 | EGFP | 1 | CMY | EGFP-N1 |
| T3-2 | EGFP | 1 | MYC | EGFP-N1 |
| T3-3 | EGFP | 1 | CMYW (SEQ ID NO: 39) | EGFP-N1 |

A quadruple URS was also investigated by modifying the residue immediately prior to the embedded T1-2 CMY to a tryptophan residue, creating the T1-4 mutant. The MWC URS was embedded in one location (T1-5). The resultant mutant had an amino acid sequence as set forth in SEQ ID NO: 3. Target 2 (GFP) was obtained by using a commercially available constitutively induced GFP bearing vector in which the CMY URS (T2-1) and/or the MYC non-URS triplet (T2-2) (as a control) were embedded in the same site (FIG. 9B). The resultant mutant had an amino acid sequence as set forth in SEQ ID NO: 38. Plasmids with WT or URS embedded target 1 sequences were transformed into the BL21 strain of E. coli (see Methods), enabling IPTG controlled gene expression. The resulting protein expression was analyzed by SDS-PAGE and immunoblotting (TB).

FIGS. 5B and 5C show the difference in the amount of target 1 protein expressed as a result of the presence of embedded URSs, which is quantified in FIGS. 5D and 5E for two different expression vectors. As can be seen clearly, all target 1 CMY mutants have significantly lower levels of protein expression. Analysis of the amount of target 1 protein within the total cell protein (without prior affinity purification) gave identical results (not shown). The position of the URS within the target has an effect on the level of translation inhibition indicating that the flanking aa sequences can relieve or exacerbate translational arrest. The T1-5 mutant has the lowest level of protein expression while the protein expression of the T1-4 mutant is greater than for that of the T1-1 mutant. These two quadruplets also indicate that the decrease in the protein production of embedded URSs is not due to codon usage of rare amino acids nor as a result of the mutagenesis process.

Example 3

Effect of the Presence of URSs on In Vitro Expression

In vitro experiments were performed to more precisely correlate the effect of the embedded URSs with the translation process. A commercial in vitro transcription/translation system was utilized and target 1 or target 2 (GFP) were expressed. The amount of either target protein (wt or mutated) could be quantified by immunoblotting and digital scanning. FIG. 5F shows the difference in the level of protein production as a result of embedding the CMY in target 1. Similar results were obtained using target 2 with embedded URSs (FIGS. 5G-I).

The presence of a URS in a highly expressed gene also inhibits ribosome recycling, causing the ribosomes to be less available for the translation of other mRNAs. This can be followed in vivo (FIG. 5J), or in a more quantitative fashion in vitro. Either target 1 or target 2 proteins were co-expressed in vitro along with the wt-GFP. The total amount of expressed protein could be quantified by immunoblotting (as shown above), however in addition, the co-expression of wt-GFP could be followed quantitatively by measuring its intrinsic fluorescence. When the mutated target 1 gene, with embedded URSs was co-expressed in the presence of the GFP encoding gene, not only was less target 1 protein observed, but the fluorescence of GFP was also significantly reduced (FIG. 10A). The same result was obtained when the T2-1 URS containing mutant protein (which was found to be non-fluorescent) was co-expressed in the presence of the wt-GFP encoding gene, while the non-URS T2-2 mutant had no effect on the wt-GFP expression (FIG. 10B).

Mutation T-10 was cloned into expression vectors (Table 2, herein above). When expression was performed in vivo as described above (FIG. 5A), and total cellular proteins were passed through a metal chelate affinity column a 12 kDa fragment was identified in the unbound fraction (FIG. 5K) that was not seen in T1-wt. A peptide of this molecular weight corresponds with about 112 aa, which would indicate that this peptide might be an arrest product directly following the position of the embedded MWC. Mass spectrometric analysis (Smoler Proteomics Center, Technion) of this fragment showed that this fragment is indeed a partial peptide of T1. Similar peptides were obtained when T1-10 was cloned into a vector that adds an 6×His tag on both N- and C-termini of the T1 protein, and in this case the fragment indeed could be affinity purified. Additional peptides were also found bound to the chelation affinity column, from the C-terminal of T1. This would appear to indicate that at least some of the fully translated protein was cleaved at specific sites by proteases, perhaps due to the arrest of T1 translation kinetics. If a nascent protein is partially synthesized, and it has now exited the ribosome, it may not be able to correctly fold and may be attacked by proteases. Continuation of translation will then create a truncated protein with a C-terminal His tag.

Example 4

Effect of the Presence of Expressed URSs on Cell Viability

Since the presence of the URSs affected the expression of both targets both in vivo and in vitro, the present inventors wanted to know if this inhibition affects cell viability.

Expression of a protein with embedded URS (T1-2) not only inhibits the production of T1, but the overall amount of protein is significantly decreased (FIG. 5J). This indicates that ribosome recycling is inhibited. In FIG. 11, results of plating cells on LB media following initiation of expression from the different plasmids are shown. E. coli cells containing the T1-wt, T1-1, T1-2, T1-5 or T1-7 plasmids were plated either in the absence or presence of IPTG. It is clear that the viability of the cells is compromised only when the URS mutations are present in the expressed protein.

Example 5

Effect of the Presence of URSs Peptides on In Vitro Translation

The present inventors next determined whether an isolated URS peptide can itself serve as an efficient inhibitor of translation (and thus as an antibiotic or antifungal agent). Preliminary in vitro studies were performed that indicate that a synthetic CMY peptide does have a greater inhibitory effect on translation of target 2 in vitro, while the synthetic MYC and AAA peptides have smaller or negligible effect on the translation of target 2 (FIG. 12).

Example 6

E. Coli URSs do not Affect Protein Translation in Proteins Expressed in Human Cells The present inventors have shown that embedding E. coli URSs in genes that are expressed in E. coli cells dramatically decreased the amount of protein expression and also reduced cell viability. In this example, they explore whether embedding these URSs in a gene that is expressed in mammalian cells would have the same effect on protein expression and cell viability. A pEGFP-N1 vector that expresses an N-terminal peptide fused to EGFP was used to follow the effect of URS presence in HeLa cells (see methods). CMY, MYC (a non-URS sequence) or CMYW (SEQ ID NO: 39) were embedded into the N-terminal encoding sequence prior to the EGFP gene by site directed mutagenesis (Table 2, herein above). Following transfection, the appearance of fluorescence within the cells was tested after 24 h and 48 h by fluorescence microscopy and by FACS analysis. The cells that carried the wt-EGFP gene indicated that the transfection was successful due to identification of fluorescent cell with microscopy and FACS analysis. FIGS. 14A-E and Tables 3 and 4, herein below show representative results of the fluorescence microscopy and FACS analysis of the expression of T3-WT, T3-1, T3-2 and T3-3 plasmids in HeLa cells.

There is no significant difference between the viability of the cells that were transfected with the wt or mutated EGFP. This result reiterates the present contention that URSs are species specific.

TABLE 3

FACS analysis of expression of EGFP or EGFP-URS mutants in HeLa cells

|  | No plasmid | T3-wt | T3-1 | T3-2 | T3-3 |
|---|---|---|---|---|---|
| % Live cells | 92.8 ± 0.2 | 88.7 ± 1.3 | 88.5 ± 0.7 | 85.6 ± 1.8 | 88.8 ± 1.0 |
| % Fluorescent live cells | 0.02 ± 0.01 | 29.1 ± 0.9 | 23.5 ± 0.7 | 24.4 ± 1.1 | 23.8 ± 0.7 |
| % Dead cells | 7.4 ± 0.2 | 11.3 ± 1.3 | 11.5 ± 0.7 | 14.4 ± 1.8 | 11.2 ± 1.0 |
| % Fluorescent dead cells | 0.0 ± 0.0 | 6.2 ± 0.9 | 3.3 ± 0.8 | 3.0 ± 0.8 | 5.0 ± 0.7 |

TABLE 4

FACS analysis of all fluorescent HeLa cells expressing EGFP or EGFP-mutants.

|  | T3-wt | T3-1 | T3-2 | T3-3 |
|---|---|---|---|---|
| % Live cells | 97.4 ± 0.3 | 98.0 ± 0.7 | 98.2 ± 0.3 | 97.4 ± 0.3 |
| % Dead cells | 2.6 ± 0.3 | 2.0 ± 0.7 | 1.8 ± 0.3 | 3.0 ± 0.3 |

Example 7

Interactions Between URSs and the Ribosomal Tunnel

The bacterial ribosomal tunnel has recently been visualized experimentally by electron microscopy [B. Seidelt, C. A. Innis, D. N. Wilson et al., *Science* 326 (5958), 1412 (2009)] showing that there are specific interactions between the nascent peptide and the tunnel and that the peptide assumes specific conformations. The coordinates of four exit tunnels have been determined by X-ray crystallography: *E. coli, D. radiodurans, H. marismortui* and *T. thermophulis*. The frequency ratio plots for all triplet aa sequences of these four organisms are presented in FIG. 5A and FIGS. 8W-Y, respectively, and they show that each of the four species has a different set of URSs. While the tunnel lining made by nucleotides from the 23S rRNA is relatively similar between the different ribosomes the three proteins that project into the tunnel contain significant differences (FIG. 13). *H. marismortui* has only two significant triplet URSs, far fewer than that of, *D. radiodurans* or *T. thermophulis*. Interestingly, the L23 protein, which in many species has an elongated loop that projects into the tunnel near its end, lacks this loop completely (FIG. 13). Additional significant changes can be seen for the two other proteins (L4 and L22) between the different organisms.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated anti-microbial peptide being between 3 and 5 amino acids, the peptide comprising the amino acid sequence CMYW (SEQ ID NO: 39).

2. The isolated peptide of claim 1, wherein said amino acid sequence is attached to a sustained-release enhancing agent selected from the group consisting of hyaluronic acid (HA), alginic acid (AA), polyhydroxyethyl methacrylate, polyethylene glycol, glyme and polyisopropylacrylamide.

3. A solid support coated with the peptide of claim 1.

4. An isolated anti-microbial peptide being 3 or 4 amino acids long, the peptide comprising the amino acid sequence selected from the group consisting of CMYW (SEQ ID NO: 39), MWC, CMW, WCM, CKW, CCY, CWM, NCW, HKC, CMC, CWW, and YWC.

5. The isolated peptide of claim 4, wherein said amino acid sequence is attached to a sustained-release enhancing agent selected from the group consisting of hyaluronic acid (HA), alginic acid (AA), polyhydroxyethyl methacrylate, polyethylene glycol, glyme and polyisopropylacrylamide.

6. The isolated peptide of claim 4, wherein the peptide comprises a sequence selected from the group consisting of CMYW (SEQ ID NO: 9) and MWC.

7. A solid support coated with the peptide of claim 4.

8. An isolated anti-microbial peptide being 3 amino acids long, the peptide comprising the amino acid sequence selected from the group consisting of WTC and DQS.

9. A solid support coated with the peptide of claim 8.

10. A method of treating a bacterial infection in a subject in need thereof, the method comprising administering to the subject a therapeutically effective amount of a peptide comprising the amino acid sequence selected from the group consisting of CMYW (SEQ ID NO: 39), PCQ, WMC, MWC, CMW, WCM, CKW, CCY, CWM, CCQ, WTC, NCW, HKC, CMC, CWW, YWC, and DQS, the peptide being no longer than 5 amino acids, thereby treating the bacterial infection.

11. The method of claim 10, wherein the bacterial infection is induced by methicillin resistant *Staphylococcus aureus* or vancomycin resistant *Staphylococcus aureus*.

12. A method of killing a microbe, the method comprising contacting the microbe with an isolated peptide comprising the amino acid sequence selected from the group consisting of CMYW (SEQ ID NO: 39), MWC, PCQ, WMC, CMW, WCM, CKW, CCY, CWM, CCQ, WTC, NCW, HKC, CMC, CWW, YWC, and DQS, the peptide being no longer than 5 amino acids, thereby killing the microbe.

* * * * *